(12) United States Patent
Vos et al.

(10) Patent No.: US 8,486,638 B2
(45) Date of Patent: Jul. 16, 2013

(54) METHOD FOR FAST DETECTION AND IDENTIFICATION OF MICRO-ORGANISMS

(75) Inventors: Pieter Vos, Rhenen (NL); Joost Thijssen, Utrecht (NL); Wouter De Levita, Utrecht (NL)

(73) Assignee: Check-Points Holding B.V., Wageningen (NL)

( * ) Notice: Subject to any disclaimer, the term of this patent is extended or adjusted under 35 U.S.C. 154(b) by 131 days.

(21) Appl. No.: 13/126,573

(22) PCT Filed: Oct. 29, 2009

(86) PCT No.: PCT/EP2009/064292
§ 371 (c)(1), (2), (4) Date: Apr. 28, 2011

(87) PCT Pub. No.: WO2010/049489
PCT Pub. Date: May 6, 2010

(65) Prior Publication Data
US 2011/0287962 A1    Nov. 24, 2011

(30) Foreign Application Priority Data
Oct. 29, 2008    (EP) .................................... 08167803

(51) Int. Cl.
*C12Q 1/68*    (2006.01)
(52) U.S. Cl.
USPC ........................................................ 435/6.12
(58) Field of Classification Search
None
See application file for complete search history.

(56) References Cited

FOREIGN PATENT DOCUMENTS
WO    WO 2004/106547 A    12/2004

OTHER PUBLICATIONS

Communication Under Rule 94(3) EPC issued in connection with European Application No. 09 752 779.0 on Feb. 23, 2012.
The International Preliminary Report on Patentability issued in connection with International Application No. PCT/EP2009/064292 on May 3, 2011.
De Bellis, G. et al., "Ligase Detection Reaction (LDR) and Universal Array (Zip Code): Application to DNA Genotyping," Minerva Biotecnologica 200212 IT, vol. 14, No. 3-4, Dec. 2002, pp. 247-252, XP008033613, ISSN: 1120-4826.
Busti, E. et al., "Bacterial Discrimination by Means of a Universal Array Approach Mediated by LDR (Ligase Detection Reaction)," BMC Microbiology, Biomed Central, London, GB, vol. 2, Sep. 20, 2002, pp. 1-12, XP002262041, ISSN: 1471-2180.
Roth, S. B., et al., "Identification of Bacteria From Positive Blood Cultures With an Oligonucleotide Array," Program and Abstracts of the Interscience Conference on Antimicrobial Agents and Chemotherapy, PY, Washington, D.C., vol. 44, Oct. 1, 2004, pp. 150-151, XP009091491, ISSN: 0733-6373.
Tobler, N. E., et al., "Rapid Detection and Species Identification of *Mycobacterium* spp. Using Real-Time PCR and DNA-Microarray," Journal of Microbiological Methods, Elsevier, Amsterdam, NL, vol. 66, No. 1, Jul. 1, 2006, pp. 116-124, XP025073212, ISSN: 0167-7012.
Monis, P. T., et al., "Emerging Technologies for the Detection and Genetic Characterization of Protozoan Parasites," Trends in Parasitology, Elsevier Current Trends, vol. 21, No. 7, Jul. 1, 2005, pp. 340-346, XP004930387, ISSN: 1471-4922.

*Primary Examiner* — James Martinell
(74) *Attorney, Agent, or Firm* — Knobbe Martens Olson & Bear LLP

(57)    ABSTRACT

The present invention relates to a specific method accomplishing fast and specific detection, identification and characterization of contaminating micro-organisms in various samples. A method has been developed based on the detection of species-specific and/or strain-specific nucleotide sequences that are uniquely identified and amplified and subsequently detected on a microarray using addressable identifier ZIP oligonucleotides. By using a two step screening process, the method of the present invention enables in first instance the fast screening of a multitude of samples for the presence or the absence of specific micro-organisms in such samples, while in a second screening step the positive results of the first step are further processed to identify and characterize the detected micro-organisms.

19 Claims, 13 Drawing Sheets

METHOD FOR FAST DETECTION AND IDENTIFICATION OF MICRO-ORGANISMS

FIELD OF THE INVENTION

Figure 1:
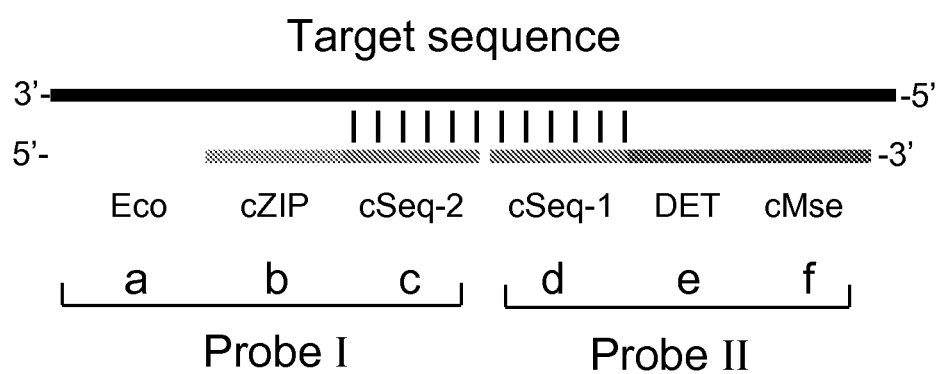

The present invention relates to a fast and efficient method for detecting the presence of micro-organisms and identifying the micro-organisms in a sample.

BACKGROUND OF THE INVENTION

Both clinical applications as well as applications in the food industry require highly efficient methods for screening samples on the presence or the absence of pathogenic micro-organisms. Whereas screening methods for clinical applications require high-throughput, fast and correct identification of the micro-organisms present in the sample for diagnostical purposes, applications in the food industry require highly reliable high-throughput methods for the microbiological control and microbiological monitoring to validate the safety and quality of food products. For both instances, methods are required that allow the fast detection, identification and characterization of micro-organisms in various samples. Other important requirements for such screening methods are the ease of use and the elimination of errors (false positives and/or false negatives).

Various screening methods known in the art such as real-time PCR enable fast screening and provide a method for testing on presence or absence of pathogenic bacteria. However, e.g., after detecting the presence of micro-organisms, further identification requires multiparameter testing, which generally cannot be provided by these screening methods. For instance, real-time PCR allows only limited multiplexing of biomarkers. In addition, detection of small changes in DNA sequences such as SNPs is often difficult.

Typical identification and characterization test methods are slow, laborious and require a high level of expertise to execute and to interpret the results. Subtyping bacteria, or determining of antibiotic resistance can only be done by classical expensive and laborious methods that require a large amount of expertise. Furthermore, the typical molecular typing methods (Ribotyping, MLST, AFLP, MLVA, MicroSeq, rep PCR etc.) require the tests to be done on pure strains. Purification of samples is often also a very tedious process, taking a long time. Many of these tests are therefore performed in specialized laboratories. The main disadvantage of this approach is that the results of the further identification of positive samples are very often too late for practical use as well as being relatively expensive, both in food and also in clinical field.

A method for efficiently screening samples on the presence or the absence of pathogenic micro-organisms and the subsequent identification of the micro-organisms has been described in EP1633887. However, a problem of the method described in EP1633887 is that all of the samples are subjected to the entire process. Even if no micro-organisms are detected, the step of screening the samples on a microarray is performed for all samples. Since generally more than 95% of food samples and water control samples are negative for the presence of micro-organisms, a lot of these samples are tested, and subjected to identification and characterization of micro-organisms which are not present in the sample. The described screening method therefore provides avoidable process steps.

In view of time and cost considerations, the present invention provides an optimized method for the detection, identification and characterization of micro-organisms in samples. The method detects in first instance whether or not micro-organisms are present in the sample and in a next step identification and characterization is carried out on the positive samples only.

SUMMARY OF THE INVENTION

The present invention relates to a specific method accomplishing fast and specific detection, identification and characterization of contaminating micro-organisms in various samples. A method has been developed based on the detection of species-specific and/or strain-specific nucleotide sequences that are uniquely identified and amplified and subsequently detected on a microarray using addressable identifier ZIP oligonucleotides (ZipComcode (cZIP) or Zipcode (ZIP)). By using a two step screening process, the method of the present invention enables in first instance the fast screening of a multitude of samples for the presence or the absence of specific micro-organisms in such samples, while in a second screening step the positive results of the first step are further processed to identify and characterize the detected micro-organisms.

FIGURES

FIG. 1: Schematic representation of target DNA and target-specific real-time ligation amplification probes.

Figure 4:
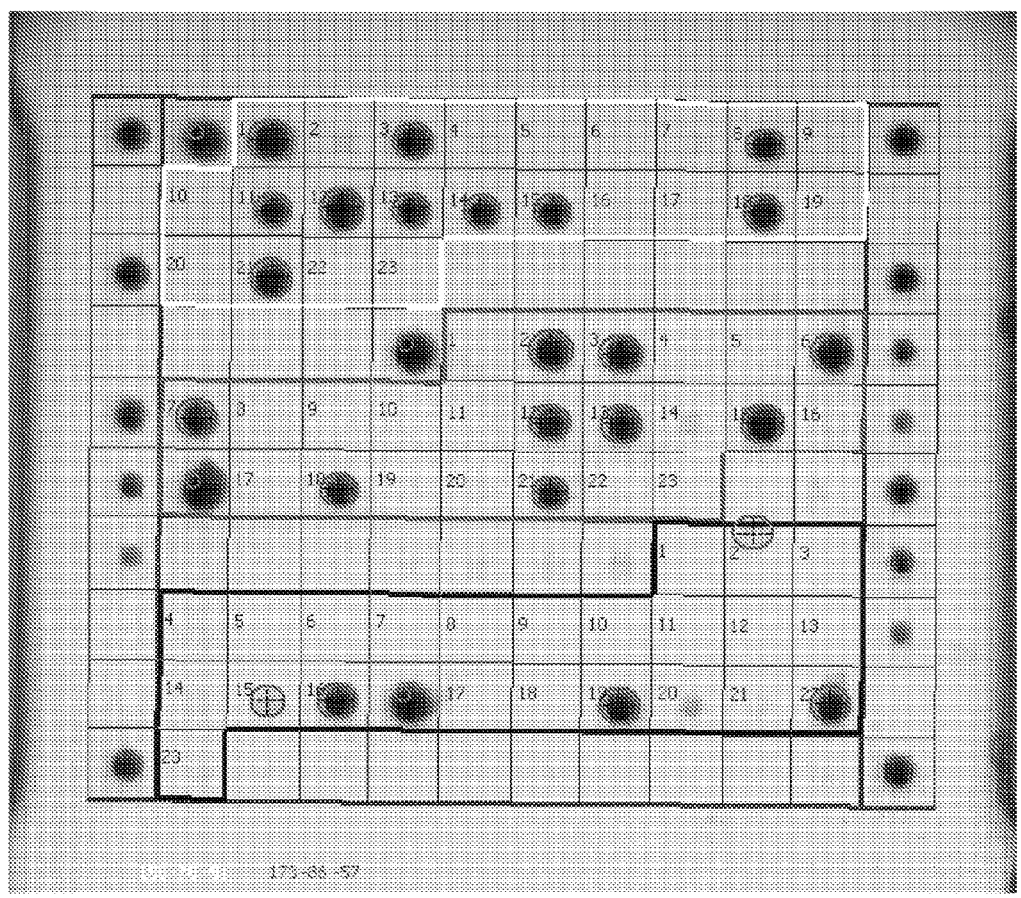

FIG. 2A shows a schematic representation of target DNA and target-specific real-time ligation amplification probes, wherein probe I and probe II are coupled. FIGS. 2B1-2B4 show that only ligated probes provide exponential amplification, which is detected by a specific detector molecule.

Figure 3:
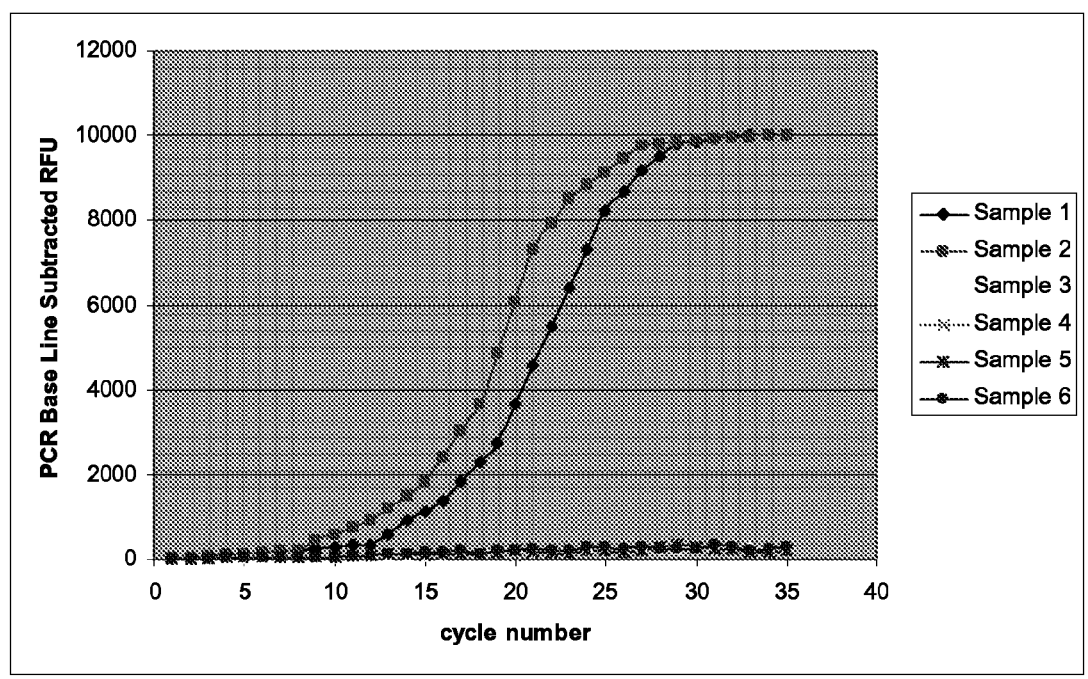

FIG. 3: Real-time LDR plots of samples 1 to 6. The X-axis displays the cycle number; the Y-axis the Relative Fluoresence Units corrected for background fluoresence. Samples 1 and 2 give a high (positive signal), indicating the presence of *Salmonella*; samples 3 to 6 give a very low signal indicating the absence of *Salmonella* in these samples.

FIG. 4: Real-time LDR reaction products of samples 1, 2 and 3 hybridized to a microarray using the PremiTest *Salmonella* detection protocol. The top panel (yellow) displays sample 1, the middle panel (green) displays sample 2, and the bottom panel (blue) displays sample 3. Samples 1 and 2 display spot pattern typical for serovars Virchow and Paratyphi B, respectively. Sample 3 displays only the amplification control spots 16, 19 and 22: this indicates that the reaction was carried out properly and that this sample does not contain *Salmonella* DNA.

Figure 5A:
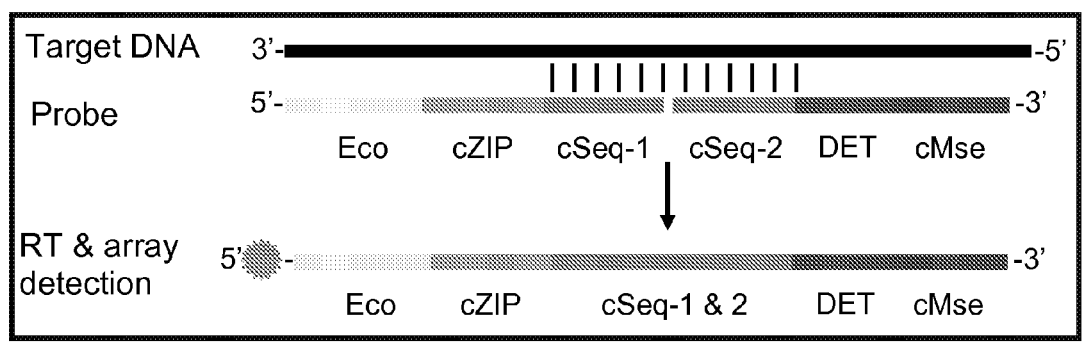
Figure 5B:
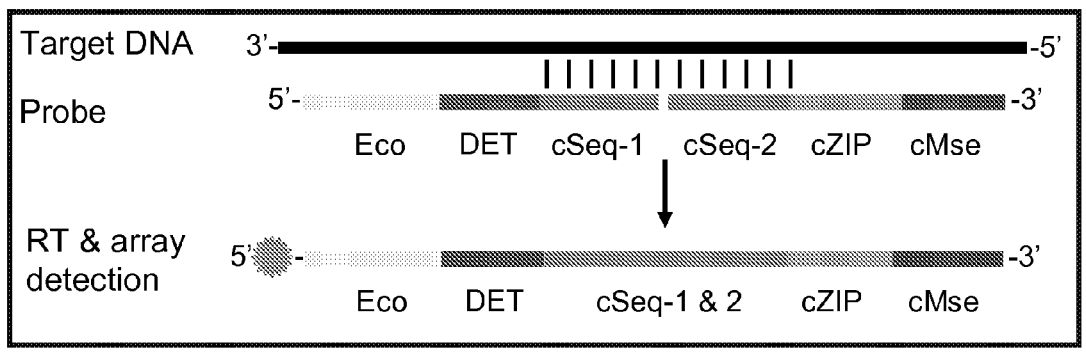
Figure 5C:
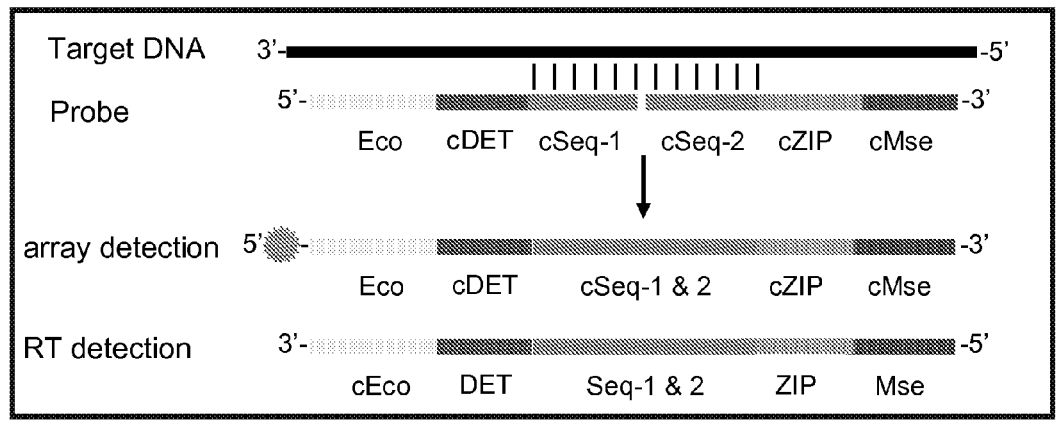
Figure 5D:
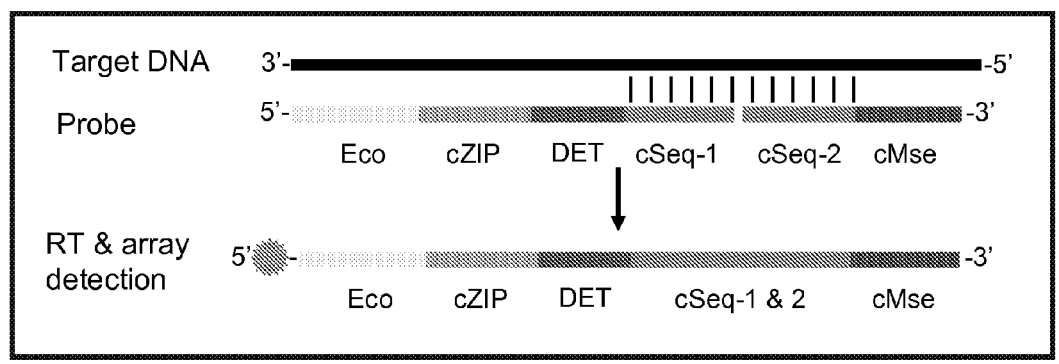
Figure 5E:
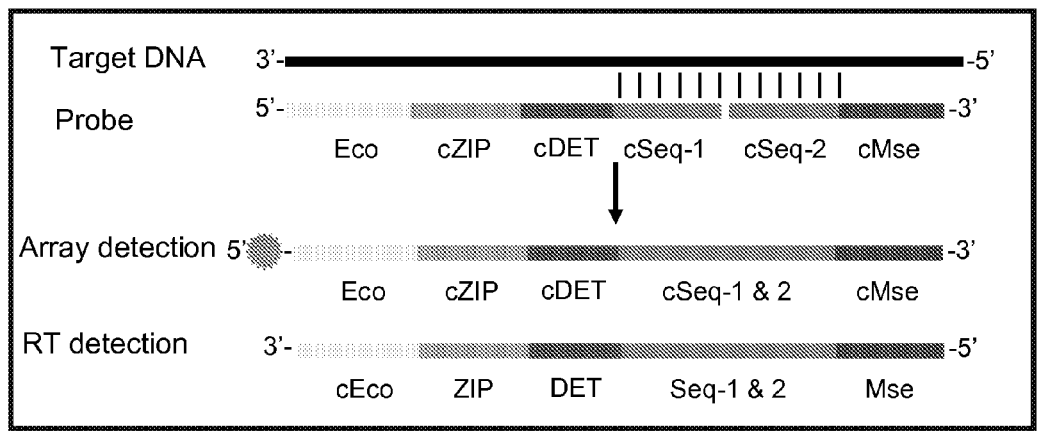
Figure 5F:
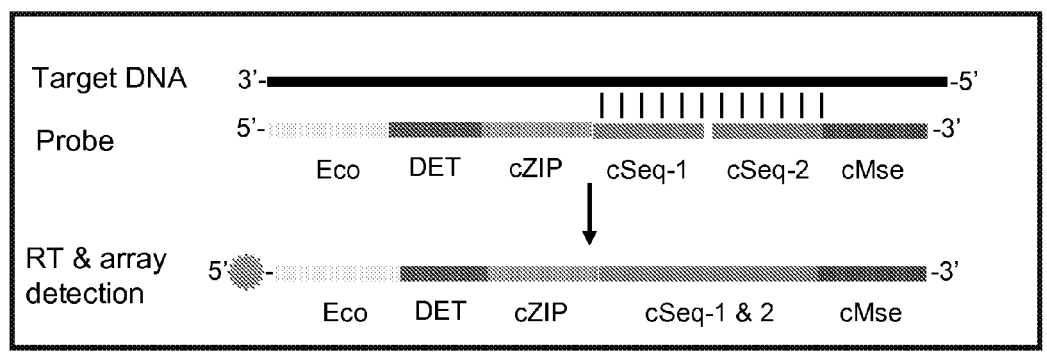
Figure 5G:
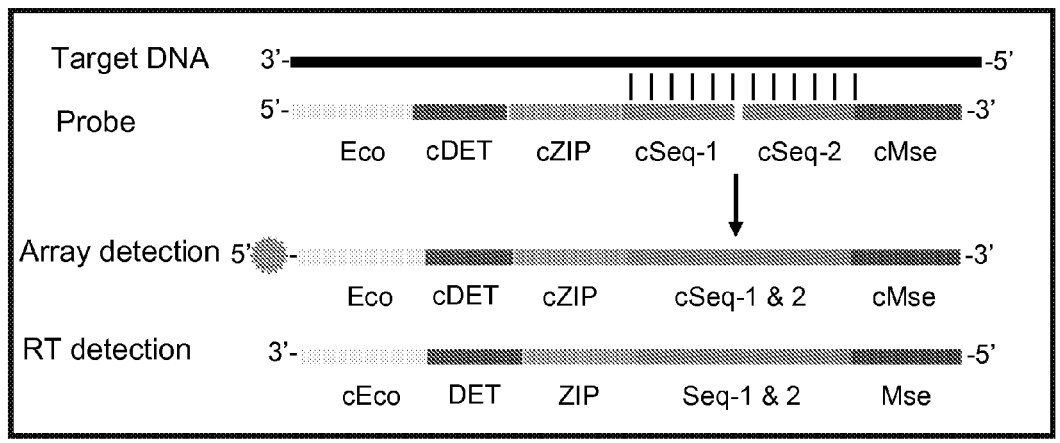
Figure 5H:
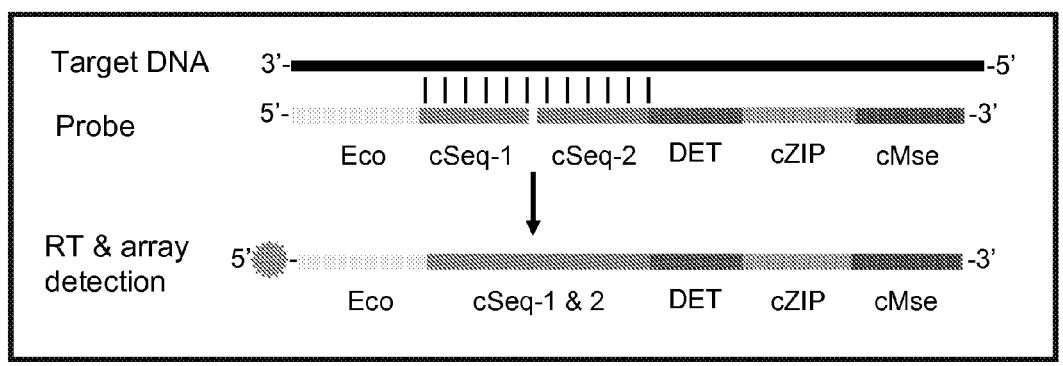
Figure 5I:
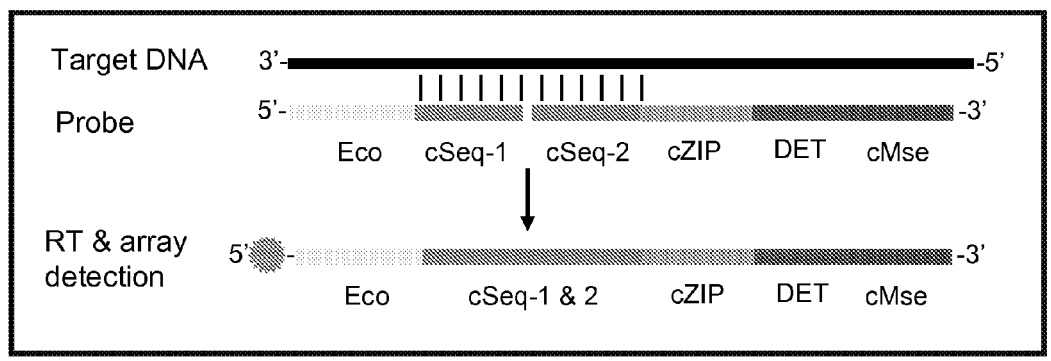
Figure 5J:
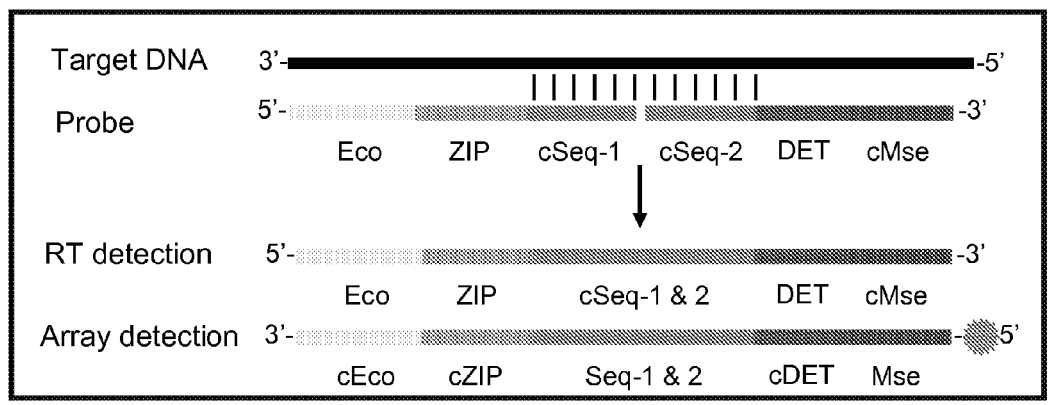
Figure 5K:
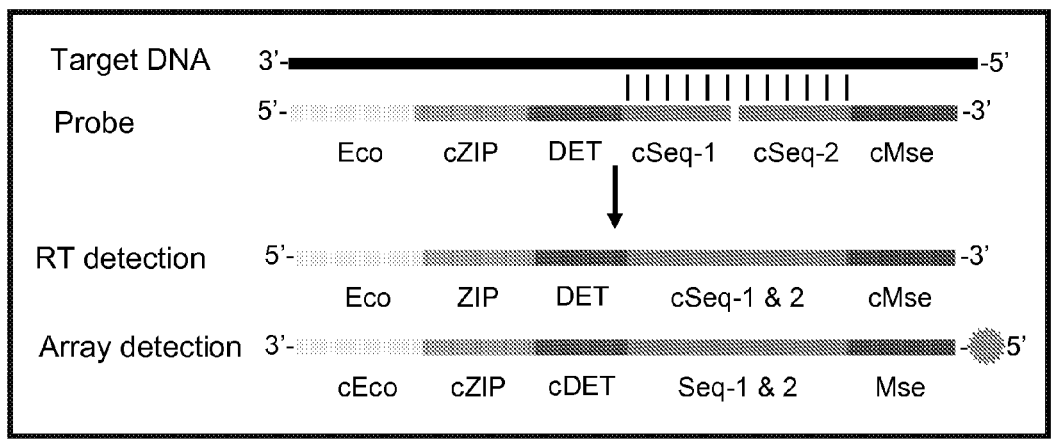
Figure 5L:
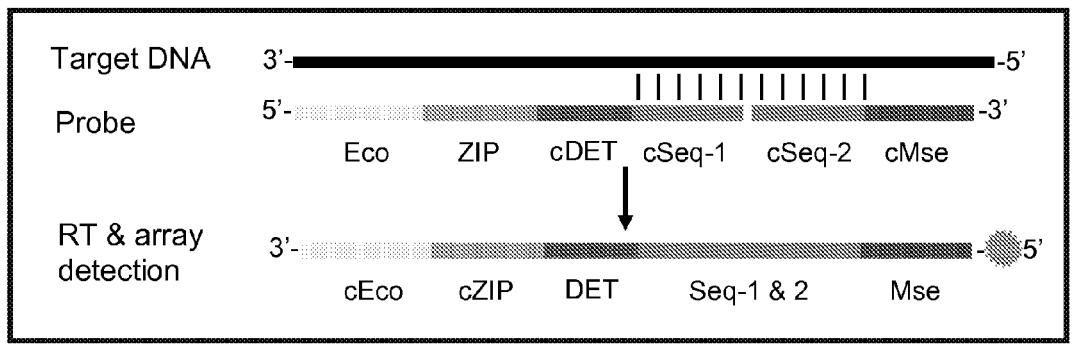
Figure 5M:
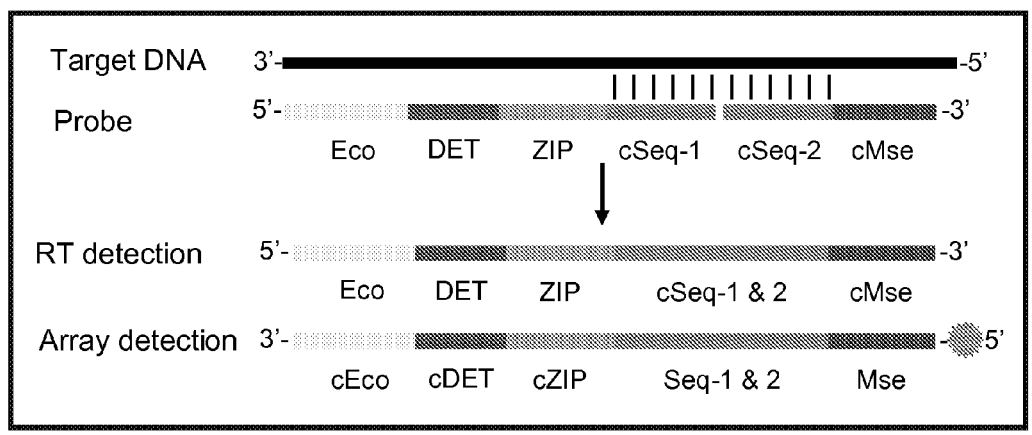
Figure 5N:

FIGS. 5a-5n show schematic representations of preferred probe pairs. Molecules resulting from amplification are depicted after the arrow. Real Time (RT) and/or microarray detection is indicated. The probe for RT detection comprises a region complementary (cDET) to the DET region. In this case, for array detection, the microarray comprises capture probes comprising a Zipcode (ZIP) essentially complementary to the ZipComcode (cZIP).

Figure 6A:
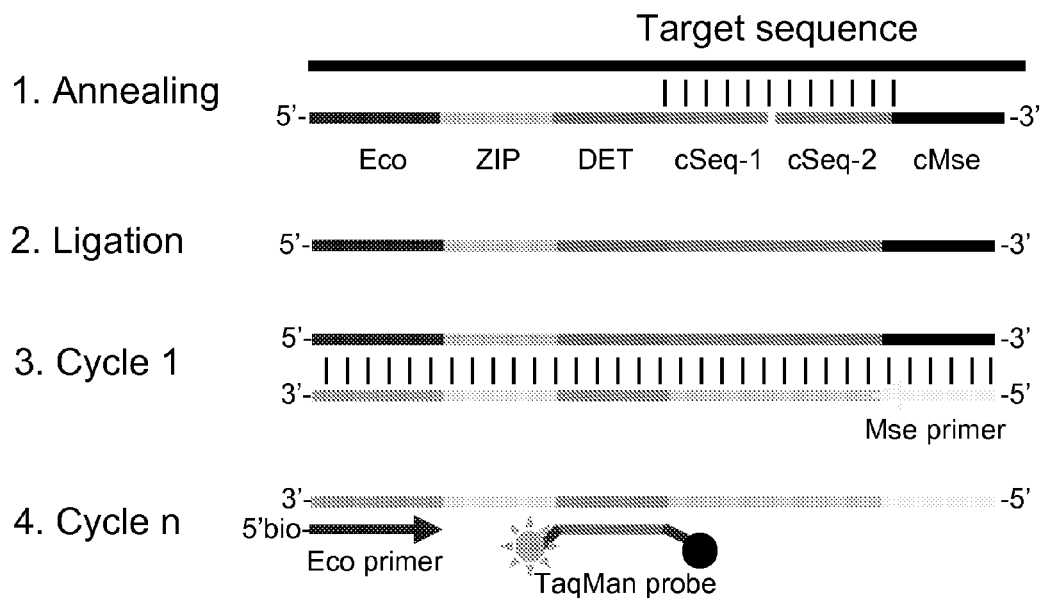
Figure 6B:
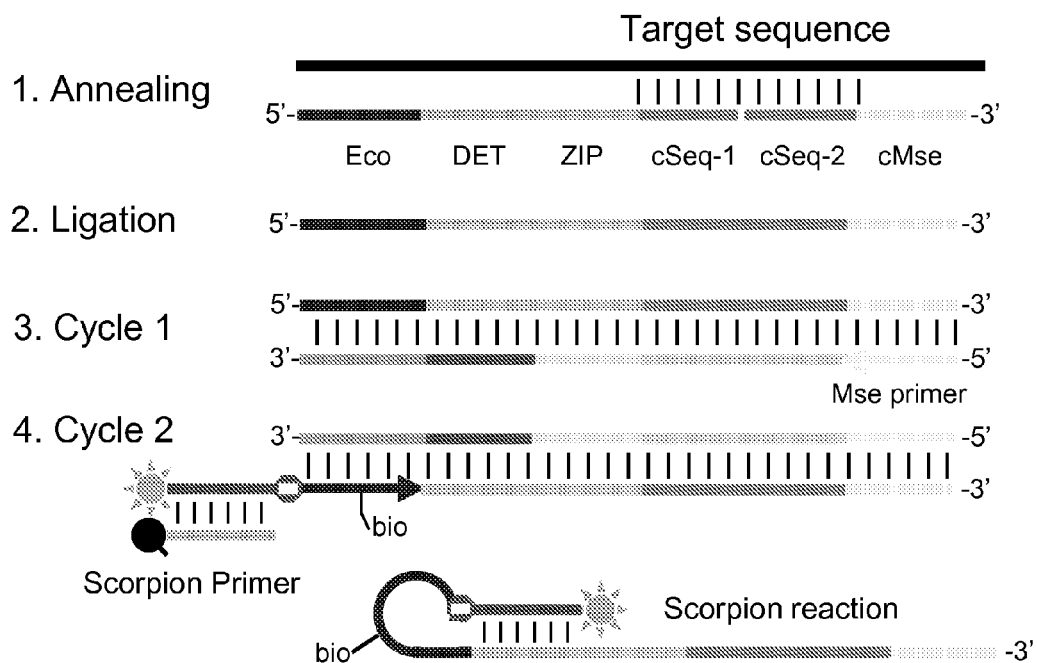
Figure 6C:
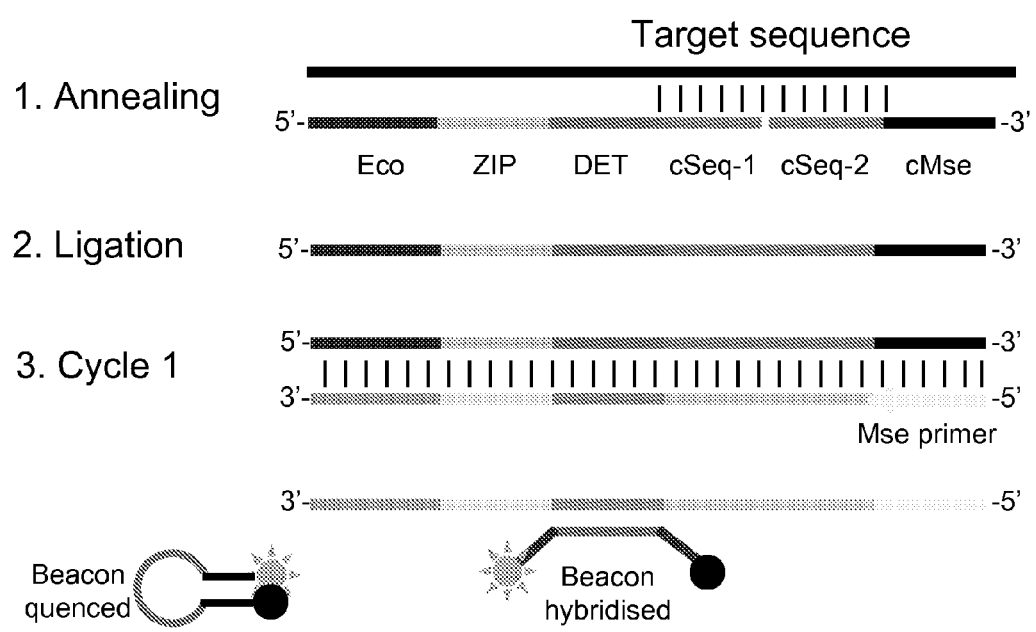

FIGS. 6a, 6b and 6c: Schematic representation of the real time detection of the amplification reaction using respectively Taqman probes, Scorpion primers and Molecular Beacon probes.

DETAILED DESCRIPTION OF THE INVENTION

The present invention relates to methods for collecting, detecting, identifying and characterizing contaminating micro-organisms in food stuffs, bodily fluids and in the control of water. More specifically, the present invention relates to a method for determining the presence and characterization of micro-organisms in a sample by using two detection steps, in which a first step comprises the detection of the presence of micro-organisms via a detector molecule, and a second step comprises the further identification and characterization of said micro-organism preferably via a labelled primer. Preferably said first step comprises monitoring the signal of detector molecules, detecting amplified target nucleic acids resulting from a ligase detection reaction in which essentially adjacent probes hybridized to a target nucleic acid are connected, and subsequently amplified. Preferably said second step comprises detecting the hybridization of amplified target nucleic acids to a capture probe.

In particular, the present invention relates to a method for determining the presence of micro-organisms in a sample and identifying and characterizing said micro-organisms, comprising the steps of:
(a) possibly extracting nucleic acids from micro-organisms, said nucleic acids comprising target nucleic acids,
(b) performing a ligase detection reaction (LDR), preferably a real-time ligase detection reaction (RT-LDR), on said target nucleic acids, comprising:
  (b1) providing a pair of a first nucleic acid probe and a second nucleic acid probe, said first nucleic acid probe comprising a 3' located target-specific sequence I complementary to a distinct part of said target nucleic acid and said second nucleic acid probe comprising a 5' located target-specific sequence II complementary to a second part of said target nucleic acid located essentially adjacent to and 3' from said target-specific sequence I, wherein said first nucleic acid probe further comprises a 5' located primer binding section I (PBS(I)) and possibly a stuffer, and said second nucleic acid probe comprises a 3' located primer binding section II (PBS(II)) and possibly a stuffer; and optionally wherein the first nucleic acid probe and/or the second nucleic acid probe further comprises at least one identifier region, such as a Zip-Comcode or Zipcode (ZIP), which (i) corresponds to a corresponding region of a capture probe on a microarray and (ii) is essentially non-complementary to said target nucleic acid, and (iii) is located in between the target specific sequence and the primer binding section,
  (b2) incubating said target nucleic acid with said first nucleic acid probe and said second nucleic acid probe under conditions allowing hybridisation of complementary nucleic acids,
  (b3) connecting any essentially adjacent probes,
  (b4) providing at least one set of two primers, wherein the first primer (primer I) is essentially identical to primer binding section I, and the second primer (primer II) is essentially complementary to primer binding section II, wherein said first or said second primer is optionally labelled, and
  (b5) amplifying any connected probe nucleic acid, wherein amplification is initiated by binding of nucleic acid primer specific for a primer binding section, thereby providing amplified target nucleic acids,
wherein one or more detector molecules, detecting the amplified target nucleic acids, are present in step (b5),
(c) monitoring the signal of said detector molecule and/or the modulation of the signal of said detector molecule, a modulation in the signal of said detector molecule indicating the presence of said target sequence whereby the presence of a micro-organism is determined,
(d) hybridizing the amplified target nucleic acids of step (c) to a capture probe, preferably present on a microarray, and said amplified target nucleic acids of step (c) optionally comprising an identifier region, such as a ZipComcode (cZIP) or Zipcode (ZIP), essentially complementary to a corresponding region of said capture probe, and,
(e) detecting the hybridized target nucleic acids of step (d), whereby the micro-organism is identified.

As the method according to the present invention determines the presence of a micro-organism using detector molecules, detecting amplified target nucleic acids, the method according to the present invention implicitly also determines the presence of specific DNA sequences present in said micro-organisms, thereby determining the presence of the micro-organism and/or specific genes of the organism, thereby further characterizing said micro-organism.

Before the present method and devices used in the invention are described, it is to be understood that this invention is not limited to particular methods, components, or devices described, as such methods, components, and devices may, of course, vary. It is also to be understood that the terminology used herein is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein may be used in the practice or testing of the present invention, the preferred methods and materials are now described.

As used herein, the terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of". The recitation of numerical ranges by endpoints includes all numbers and fractions subsumed within the respective ranges, as well as the recited endpoints. The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed. All documents cited in the present specification are hereby incorporated by reference in their entirety.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention.

In the present specification and the appended claims, the singular forms "a", "an", and "the" include the plural references, and vice versa, unless the context clearly indicates otherwise. Unless defined otherwise, all technical and scientific terms used herein have the same meaning as commonly understood by one of ordinary skill in the art.

In general, a sample or specimen will be taken as a part of anything. For applications in the food industry such samples are for instance food stuffs, dairy products, beverages and beer being produced presented for inspection, or shown as evidence of the quality of the whole. For clinical applications the sample or specimen can be any kind of bodily solid, semi-solid or fluid substance such as, but not limited to faeces, blood, blood plasma, serum, urine, bodily liquid, rectal swabs, nasal swabs, sputum, infected tissue, etc.

In one aspect of the invention, the present method is applicable to the micro-organisms which are known to contaminate food stuffs, dairy products, beer and other beverages, for example the micro-organisms presented herein. Alternatively, according to another aspect of the present invention, the present method is applicable to the micro-organisms which are known to cause infections and maladies.

As such, the present invention relates to a method for determining the presence of micro-organisms in a sample, comprising the steps of optionally collecting said micro-organisms if present, extracting nucleic acids from said micro-organisms, specifically amplifying said nucleic acids thereby detecting the amplified target nucleic acids, whereby the presence of said micro-organisms is determined. For samples where the presence of said micro-organisms is detected, the amplified nucleic acids are further analyzed, thereby identifying and characterizing the present micro-organisms. As a consequence, only the positive samples are subjected to a further analysis which constitutes in a time, work and/or material saving method.

As will be evident, the present invention relates to a method as described herein, wherein said micro-organism is selected from the group consisting of eukaryotic and/or prokaryotic micro-organisms as well as viruses. The micro-organism may be selected from the group comprising algae, archaea, bacteria, viruses, nematodes, protozoa, microsporidae and fungi including yeasts, moulds and mycorrhizae.

Similarly, it will be appreciated that the present invention relates to a method as described herein, wherein said micro-organism is selected from the group consisting of food borne and waterborne micro-organisms.

Similarly, it will be appreciated that the present invention relates to a method as described herein, wherein said micro-organism is selected from the group consisting of human and/or animal parasitic, symbiotic, commensals and/or pathogenic micro-organisms.

In this respect, the present invention relates to a method as described herein, wherein said micro-organism is selected from:
the group of bacteria and (sub)species thereof consisting of *Escherichia, Salmonella, Shigella, Klebsiella, Citrobacter, Serratia, Averyella, Hafnia, Morganella, Pantoea, Photorhabdus, Pleosimonas, Proteus, Providencia, Raoultella, Edwardsiella, Ewingella, Cedecea, Kluyvera, Leclercia, Leminorella, Moellerella, Rahnella, Tatumella, Yokenella, Enterobacter, Yersinia, Nocardia, Rhodococcus, Gordonia, Actinomadura, Streptomyces, Mycobacterium, Propionibacterium, Actinomyces, Lactobacillus, Eurobacterium, Eggerthella, Olsenella, Bifidobacterium, Mobiluncus, Alistipes, Bacteroides, Cetobacterium, Desulfovibrio, Dialister, Faecalibacterium, Fusobacterium, Porphyromonas, Prevotella, Sneathia, Tannerella Lactococcus, Listeria, Erysipelothrix, Leuconostoc, Bacillus, Staphylococcus, Clostridium, Vibrio, Enterococcus, Legionella, Campylobacter, Arcobacter, Helicobacter, Leptospira, Borrelia, Treponema, Mycoplasma, Ureoplasma, Chlamydia, Chlamydophila, Rickettsia, Orientia, Ehrlichia, Anaplasma, Neorickettsia, Aegyptianella, Coxiella, Tropheryma, Streptococcus, Micrococcus, Pseudomonas, Flavobacterium, Alcaligenes, Microbacterium, Neisseria, Actinobacillus, Capnocytophaga, Eikenella, Kingella, Pasteurella, Haemophilus, Aeromonas, Burkholderia, Stenotropomonas, Ralstonia, Cupriavidus, Pandoraea, Brevundimonas, Comamonas, Delftia, Acidovorax, Acinetobacter, Achromobacter, Chryseobacterium, Moraxella, Bordetella, Psychrobacter, Oligella, Haematobacter, Alcaligenes, Advenella, Alishewanella, Aquaspirillum, Laribacter, Myroides, Shewanella, Ochrobactrum, Rhizobium, Halomonas, Herbaspirillum, Inquilinus, Massilia, Sphingobacterium, Pedobacter, Paracoccus, Asaia, Methylobacterium, Roseomonas, Azospirillum, Elizabethkingia, Empedobacter, Weeksella, Bergeyella, Balneatrix, Bordetella, Francisella, Brucella, Bartonella, Peptostreptococcus, Finegoldia, Anaerococcus, Peptoniphilus, Veillonella, Gallicola, Sackia, Atopobium, Ruminococcus, Aerococcus, Abiotrophia,*
the group of viruses consisting of: Human Immunodeficiency Viruses (HIV), Humman T-Cell Lymphotropic Viruses, Influenza Viruses, Parainfluenza Viruses, Mumps Virus, Respiratory syncytial virus, Human metapneumoviruses, Measles Virus, Rubella virus, Enteroviruses, Pareochviruses, Hepato viruses, Rhinoviruses, Coronaviruses, Rotaviruses, Caliciviruses, Astroviruses, Adenoviruses, Coronaviruses, Toroviruses, Aichi Virus, Picobimaviruses, Rabies virus, Hendra and Nipah Viruses, Arboviruses, Hantaviruses, Arenaviruses, Filoviruses, Human Herpesviruses, Human Papillomaviruses, Human Polyomaviruses, Human Paroviruses, Poxviruses, Hepatitis Viruses
the group of Fungi consisting of: *Candida, Cryptococcus, Blastoschizomyces, Clavispora, Debaryomyces, Kluyveromyces, Geotrichum, Ustilago, Prototheca, Dipodascus, Malassezia, Pichia, Rhodotorula, Saccharomyces, Sporobolomyces, Trichosporon, Pneumocystis, Aspergillus, Fusarium, Scedosporium, Penicillium, Scopulariopsis, Chaetomium, Schizophyllum, Acremonium, Lecythophora, Phialemonium, Phaeoacremonium, Arthrographis, Onychocola, Scytalidium, Beauveria, Engyodontium, Sporothix, Chrysosporium, Myceliophthora, Myriodontium, Metarrhizum, Trichoderma, Paecilomyces, Rhizopus, Rhizomucor, Absidia, Apophysomyces, Mucor, Cunninghamella, Basidiobolus, Conidiobolus, Mortierella, Cokeromyces, Syncephalastrum, Saksenaea, Histoplasma, Blastomyces, Coccidioides, Paracoccidioides, Emmonsia, Trichophyton, Microsporum, Epidermophyton, Malassezia, Piedraia, Calosphaeriales, Chaetothyriales, Dothideales, Microascales, Ophiostomatales, Pleosporales, Sordariales, Hypocreales, Diaporthales*, and/or
the group of parasites consisting of: *Plasmodium, Babesia, Leishmania, Trypanosoma, Toxoplasma, Naegleria, Acanthamoeba, Balamuthia, Entamoeba, Endolimax, Iodamoeba, Blastocystis, Giardia, Dientamoeba, Trichomonas, Chilomastix, Enteromonas, Retortamonas, Isospora, Cyclospora, Sarcocystis, Cryptosporidium, Microsporidium.*

In a particular embodiment of the present invention the micro-organisms are captured or collected prior to step (a) of the method of the present invention. The capturing or collection of the micro-organisms prior to step (a) of the method provides a concentration step which allow a concentration of the micro-organisms prior to the method of the invention, thereby providing a more accurate method.

In order to increase the amount of micro-organisms present in a sample, said micro-organisms, if present, may be grown on media. Accordingly, the present invention relates to a method as described herein, wherein said method, for instance step (a) of above, is preceded by an enrichment of micro-organisms, comprising (i) growth of said micro-organisms on selective media, or (ii) growth of said micro-organisms on non-selective media. Growth of said micro-organisms on selective media will preferably favour the growth of micro-organisms of interest, while the growth on non-selective media will sustain growth of most micro-organisms, e.g. not especially favouring the growth of a particular micro-organism.

Although the sample can be used directly for DNA-isolation, some techniques require the growth and collection of the micro-organisms prior to the DNA-isolation. According to the method of the invention the growth and collection of the micro-organisms prior to the DNA-isolation is not required nor essential, thereby providing a faster detection method compared to the prior art methods. The growth and collection of the micro-organisms prior to the DNA-isolation may however be optionally included in the method of the invention. Accordingly, the present invention relates to a method as described herein, wherein said method, for instance step (a) of above, is preceded by an enrichment of micro-organisms, comprising concentrating the micro-organisms. Typical collection strategies known in the art are for instance, but not limited to, plating out the sample on a suitable solid culture medium, adding the sample in a suitable liquid culture medium or first providing the sample in a suitable liquid culture medium followed by plating it out on a suitable solid culture medium. From a solid culture medium, micro-organisms can be directly collected for DNA-isolation, while a liquid culture medium in general requires first a centrifugation step to collect the micro-organisms. The collection and/or capturing of said micro-organisms may be performed by means of centrifugation, filtration, such as filtering of an aqueous or liquid solution, whereby all particles larger than the sieving size are being captured, sedimentation, electrostatic forces, coagulation, flocculation, capturing of micro-organisms by antibodies, and/or capturing of micro-organisms by ligands.

Other collection and/or capturing techniques may include microfiltration ad preferably membrane microfiltration such as the Micro Analytical Screen (MAS) method. This method achieves low flow resistance, a high chemical resistance and a well controlled pore size distribution of the membrane filters, in order to obtain a high operational flux, long standing times (e.g. a long life/operation time of the microsieve) and good separation behaviour. Preferably, the microsieve filters according to the present invention are characterised by thin membrane layers with uniformly sized pores. For most applications, the membrane layer is sustained by a support. A microsieve having a relatively thin filtration or sieving layer with a high pore density and a narrow pore size distribution on a macroporous support will show a satisfactory to good or even excellent separation behaviour and a high flow rate. In very dilute suspensions, it will be important to have a fast determination of the kind and concentration of particles, such as for example fruit juices contaminated with micro-organisms. The low flow resistance of the microsieve allows a large amount of liquid to pass through the filter in a small amount of time, whereby the contaminating micro-organisms (if present) are concentrated on a very small surface (20-100 $mm^2$). This fast concentration of the contaminating micro-organisms adds in simplifying and the quality of the subsequent analysis of these micro-organisms. With regard to the microfiltration technology, the present invention relates also to cross-flow microfiltration as described by Daufin et al. (2001), to a microfiltration technology described by the patent application WO 02/43937 (by Aquamarijn Holding Ltd.), or to a microfiltration technology developed by CEPAration B.V. (Helmond, The Netherlands). Accordingly, the present invention relates to a method as described herein, wherein said filtration is performed by using an Aquamarijn® filter or a CEPAration® filter. For instance, silicon nitride may be used as membrane, and silicium as carrier, or the filter may comprise a hollow fibre ceramic membrane. The size of pores may for instance be between 0.5 and 1.2 micron or between 0.15 and 1.4 micron.

It will be understood that the present invention relates to a method as described herein, wherein said concentrating is followed by separating the micro-organisms from the remainder of the sample. In addition, concentrating and separating may be performed simultaneously, thereby increasing the velocity of the analysis.

A wide variety of colouring and/or staining techniques can be used in order to improve the recognition of the micro-organisms on the microsieve surface. Microsieves are preferably inert which makes it possible to use all present staining agents and chemicals without colouring or attacking the microsieve surface. Said microsieve may be used again.

The presented MAS method may also be applied for the quality control of water in general and drinking water in particular on the presence of contaminating micro-organisms, such as, for example, *Cryptosporidium*, *Escherichia coli* and *Legionella*. Also in the meat industry, the MAS method can be applied to trace contaminating micro-organisms, such as, for example, *Campylobacter* and *Salmonella* contaminations.

In order to characterise the contaminating micro-organism, the present invention may employ known techniques identifying the nucleic acid of the micro-organism at issue. The present invention relates preferably to the multiplexed amplification and labelling technique described below. Multiplexing provides the opportunity to perform multiple analyses during a single process step providing faster analysis times and lower amounts of consumables to be used.

The term "nucleic acid" as used herein means a polymer composed of nucleotides, e.g. deoxyribonucleotides or ribonucleotides. The terms "ribonucleic acid" and "RNA" as used herein means a polymer composed of ribonucleotides. The terms "deoxyribonucleic acid" and "DNA" as used herein means a polymer composed of deoxyribonucleotides. The terms "oligonucleotide", "primer" and "probe" as used herein denotes single stranded nucleotide multimers of from about 10 to about 250 nucleotides in length. The term "polynucleotide" as used herein refers to single or double stranded polymer composed of nucleotide monomers of from about 10 to about 250 nucleotides in length, usually of greater than about 250 nucleotides in length up to about 2000 nucleotides in length.

It will be understood that the present invention relates to a method as described herein, wherein said nucleic acids are chosen from the group consisting of DNA, rRNA, tRNA, siRNA, mRNA, total RNA and tmRNA (dual tRNA-like and mRNA-like nature; also known as 10Sa RNA or SsrA).

In order to characterise the nucleic acid from a contaminating micro-organism, i.e. the target nucleic acid, said nucleic acid is normally isolated from the contaminating micro-organism after said organism has optionally been collected or captured. The collection or capturing of the contaminating organism and the isolation of the nucleic acids are performed using generally known techniques. In general, isolation of nucleic acids from micro-organisms requires as one of the first steps the lysis of said micro-organism. It will be apparent that the cell lysis strategies employed are dependent of the nature of the contaminating micro-organisms. In general, a treatment with a lysozyme, a pectinolytic, or a mechanical treatment such as sonication or a bead beater can be used for lysing the cells. A customary procedure is the direct injection of bacterial samples into a hot phenol solution, such as described by Selinger et al. (2000, Nature Biotechnol. 18, 1262-1268), which is incorporated herein by reference. Alternatively, cells can be quickly frozen in liquid nitrogen and mechanically broken before isolation with an acid phenol solution. Classical methods for isolating nucleic acids relating to combinations of enzymatic degradation, organic extraction and alcohol and/or salt precipitation are well known in the art, and contemplated by the present invention. In this regard, the techniques for isolating ribonucleic acids as described in Current Protocols in Molecular Biology, Wiley & Co, USA are especially incorporated herein by reference. The present invention also relates to rapid small scale purification of DNA and RNA from clinical samples. The latter method may be based on the lysing and nuclease inactivating properties of the chaotropic agent guanidinum thiocyanate (GuSCN) and the nucleic acid-binding properties of silica particles or diatoms in the presence of this agent, such as described by Boom et al. (1999; J. Clin. Microbiol. 37: 615-619). For the isolation of RNA typical techniques known in the art can be used. Most microbial mRNA species only have a half-life of minutes, mainly due to the activity of RNases. Therefore, the speed required to stabilize the RNA population, i.e. to arrest or decrease RNA degradation, becomes crucial and therefore the use of various inhibitors of ribonuclease activity, such as, for example, diethylpyrocarbonate, aurintricarboxylic acid, etc, may be employed in RNA isolation procedures, and belong to the common, general knowledge regarding isolation of RNA, and are incorporated herein. The lysis of said contaminating micro-organism may be performed before or after stabilising the nucleic acid population. The present invention relates also to a stop solution containing ethanol and phenol, as has been described for the isolation of total RNA from E. coli (Ye et al., 2001, J. Microbiol. Methods 47, 257-272). This stop solution may be used successfully for other Gram negative bacteria. In addition, the present invention contemplates the use of the RNAlater® solution (Ambion and Qiagen). The main advantage of the latter solution is its rapid stabilisation of the mRNA population, allowing the samples to be stored for a long period of time under appropriate conditions prior to RNA isolation. It is especially useful for the collection of samples when immediate isolation of RNA is not possible. Accordingly, the present invention relates to a method as described herein, wherein said step of extracting nucleic acids from said micro-organisms comprises lysing the micro-organisms, and optionally further inactivating RNAses.

As most of the mRNAs of bacteria do not have a poly A+ tail and are therefore difficult to separate from the total RNA, an enrichment step may be used. The present invention relates to an enrichment step for mRNA, by removing the ribosomal RNA as known in the art, e.g., as described by Affymetrix (http://www.affymetrix.com/index.affx). In addition, the present invention incorporates a method to isolate E. coli mRNA by polyadenylating it in crude cell extracts with poly A+ polymerase I from E. coli and purifying it by oligo-dT chromatography as described by Wendisch et al. (2001 Anal. Biochem. 290: 205-213), incorporated herein by reference.

A variety of RNA isolation kits are available from different commercial sources, e.g. from Ambion, Qiagen, Sigma-Aldrich and others, which may successfully be used in the method of the present invention.

As described above for isolating RNA, in isolating DNA the method to lyse the micro-organism depends on the type of micro-organism, e.g. moulds, fungi, yeast, Gram negative or Gram positive bacteria. In this regard, the techniques for isolating DNA as described in Current Protocols in Molecular Biology, Wiley & Co, USA are especially incorporated herein by reference. Accordingly, the present invention relates to a method as described herein, wherein said lysing is chosen from the group consisting of a treatment with a lysozyme, a pectinolytic, or guanidinium thiocyanate or by a mechanical treatment such as sonication or the use of a bead beater, by injecting the micro-organisms in hot phenol, and snap freezing the micro-organisms in liquid nitrogen followed by a mechanical treatment. A convenient method for isolating RNA from Gram negative organisms is to resuspend the cells in water and boil the water for at least one minute. Optionally EDTA and/or a detergent can be added to the water.

A variety of genomic DNA isolation kits are available from different commercial sources, e.g. from Gentra, Promega, Qiagen and others, which may successfully be used in the methods of the present invention.

A convenient way to estimate the concentration of the isolated nucleic acid is by spectrophotometry at 260 nm, which is well known in the art.

After nucleic acids have been isolated from the contaminating micro-organisms, said nucleic acids need to be detected and possibly analysed. In general, only minute amounts of contaminating micro-organisms are present. Therefore, the isolated nucleic acids or a specific portion thereof, i.e. the target nucleic acid, may be amplified. In case of the target nucleic acid being RNA, said RNA may first be converted to cDNA before analysis. It will be understood that the terms "amplified nucleic acids" and "amplified nucleic acid mixture" as used throughout the invention have essentially the same meaning.

Therefore, the present invention relates to a method as described herein, wherein said nucleic acid is rRNA, tRNA, mRNA, siRNA, total RNA, or tmRNA and wherein said rRNA, tRNA, mRNA, siRNA, total RNA, or tmRNA is converted to cDNA, e.g. by the activity of a reverse transcriptase, as is well known in the art.

Various techniques are known by the person skilled in the art to amplify DNA and/or cDNA. All of these techniques are contemplated by the present invention. Accordingly, the present invention relates to a method as described herein, wherein said nucleic acid is DNA and/or cDNA, and wherein said DNA and/or cDNA is amplified using an amplification technique such as bDNA, Hybrid capture, SDA, TMA, PCR, LCR, TAS, 3SR, NASBA and Qβ amplification, as explained in Versalovic and Lupski (2002, Trends Microbiology 10: S15-S21), which is incorporated herein by reference.

The present invention especially contemplates multiplex amplification, such as multiplex PCR. Multiplex amplification, such as multiplex PCR, allows amplification, and thus analysis of two or more targets simultaneously. This amplification technique is used for genetic screening, micro satellite analysis, and other applications where it is necessary to amplify several products in a single reaction. By routine experimentation the person skilled in the art will be able to optimize the reaction conditions, in view of having multiple primer pairs in a single reaction, which may increase the likelihood of primer-dimers and other nonspecific products that may interfere with the amplification of specific products. In addition, the concentrations of individual primer pairs often need to be optimized since different multiplex amplicons are often amplified with differing efficiencies, and multiple primer pairs can compete with each other in the reaction. The person skilled in the art will make similar considerations and optimize the conditions for the other amplification techniques described above for multiplex amplifications, i.e. amplification of more than one target.

In addition, the present invention relates to the direct amplification of RNA, such as, for example, via a modified Tyras method, wherein a primer/probe comprising a RNA polymerase recognition site and recognition site complementary to the target nucleic acid is used.

After isolating the target nucleic acid, probes and/or primers are hybridised to the said target nucleic acid. The primers may be used to amplify the said target nucleic acid. Alternatively, the probes may be ligated and may be amplified with primers specifically recognising regions on said probes. The probes and/or primers may be labelled. Also, the label may be incorporated during the amplification step or attached after amplification. Accordingly, the present invention relates to a method as described herein, wherein the amplified nucleic acid is labelled. Virtually any label that produces a detectable and/or quantifiable signal and that is capable of being attached to or incorporated into the amplified nucleic acid, can be used in conjunction with the methods and arrays of the invention. Suitable labels include, by way of example and not limitation, radioisotopes, fluorophores, chromophores, chemiluminescent moieties, etc. In embodiments where the label is attached to the amplified nucleic acid, the label can be attached to any part of the nucleic acid, including the free terminus or one or more of the bases. Preferably, the position of the label will not interfere with hybridisation, detection and/or other post-hybridisation modifications of the labelled nucleic acid. A variety of different protocols may be used to generate the labelled nucleic acids, as is known in the art, where such methods typically rely on the enzymatic generation of labelled nucleic acid using an initial primer and template nucleic acid. Labelled primers can be employed to generate the labelled amplified nucleic acid. Alternatively, label can be incorporated into the nucleic acid during first strand synthesis or subsequent synthesis, labelling or amplification steps in order to produce labelled amplified nucleic acid. Label can also be incorporated directly to mRNA using chemical modification of RNA with reactive label derivatives or enzymatic modification using labelled substrates. Representative methods of producing labelled amplified nucleic acid are disclosed in U.S. application Ser. Nos. 08/859,998; 08/974,298; 09/225,998; the disclosures of which are incorporated herein by reference.

The amplified nucleic acids may be labelled, for example, by the labels and techniques described supra. Alternatively, they may be labelled by any other technique known in the art. Preferred techniques include direct chemical labelling methods and enzymatic labelling methods, such as kinasing and nick-translation. Accordingly, the present invention relates to methods as described herein, wherein the amplified target nucleic acid is labelled. Preferably, the nucleic acid is labelled during amplification, or the amplified target nucleic acid is labelled after amplification. As such, the present invention relates to methods as described herein, wherein primer I and/or primer II are labelled. Labelling during amplification provides faster analysis times as it provides the opportunity to eliminate a process step where the amplified targets are labeled.

A variety of different labels may be employed, where such labels include fluorescent labels, phosphorescent labels, isotopic labels, enzymatic labels, particulate labels, etc. For example, suitable labels include fluorochromes, e.g. fluorescein isothiocyanate (FITC), rhodamine, such as rhodamine 123, R6G, IRDyes™, Texas Red, phycoerythrin, allophycocyanin, 6-carboxyfluorescein (6-FAM), 2',7'-dimethoxy-4',5'-dichloro-6-carboxy-fluorescein (JOE), 6-carboxy-X-rhodamine (ROX), TET, JOE, NED, (ET-)ROX, 6-carboxy-2',4',7',4,7-hexachloro-fluorescein (HEX), 5-carboxyfluorescein (5-FAM) or N,N,N',N'-tetramethyl-6-carboxyrhodamine (TAMRA), fluor 488™, cyanine dyes, e.g. Cy5, Cy3, Cy2, BODIPY dyes, e.g. Biodipy™ 630/650, Biodipy 530, Biodipy™ FL, Alexa such as Alexa542, Alexafluor™ 532, etc. Suitable isotopic labels include radioactive labels, e.g. $^{32}P$, $^{33}P$, $^{35}S$, $^{3}H$. Other suitable labels include size particles that possess light scattering, fluorescent properties or contain entrapped multiple fluorophores. The label may be a two stage system, where the primer and/or probe is conjugated to biotin, haptens, etc. having a high affinity binding partner, e.g. avidin, specific antibodies, etc. The binding partner is conjugated to a detectable label, e.g. an enzymatic label capable of converting a substrate to a chromogenic product, a fluorescent label, an isotopic label, etc.

In certain embodiments, the primers directed to different target nucleic acids may be differentially labelled. By "differentially labelled" and "contain a different label" is meant that the primers directed to different target nucleic acids are labelled differently from each other such that they can be simultaneously distinguished from each other. Hence, primer I may contain a label different from primer II. For instance, primer I or primer II binding to a first pair of probes, may contain a different label from primer I or primer II binding to a second pair of probes.

An embodiment of the invention relates to the combination of (1) multiplex Ligase Detection Reaction (LDR) and (2) multiplex Polymerase Chain Reaction (PCR). The Ligase Detection Reaction (LDR) is a sensitive assay for detecting Single Nucleotide Polymorphisms (SNPs), as described by Favis et al., (2000, Nature Biotechnology 18: 561-564), incorporated herein by reference. A difference in a single nucleotide along the 16S rRNA may be employed to distinguish between sequences of different micro-organisms, as described by Busti et al. (2002, BMC Microbiology 2: 27-39), which is incorporated herein by reference. Similarly, single nucleotide differences along the 18S, 23S or 28S rRNA may be employed to distinguish between sequences of different micro-organisms. Similarly, any nucleotide difference between two organisms in any type of DNA or RNA, such as chromosomal DNA, rDNA, plasmid DNA, mitochondrial DNA or any other organel DNA, rRNA, mRNA, tRNA or any other RNA molecule such as described infra, may be employed to distinguish between micro-organisms. A set of two probes (probe I and II) may be designed, based on the target sequence to be detected, of which at least a part is known. Both probes contain a region at the end (the 3' and the 5' end of the respective probes I and II) that is capable of hybridizing to the known section of the target sequence. In other words, one probe (probe I) comprises a region Ir or tss(I) (specifically hybridising to a target region, said region Ir or tss(I) being located at the ultimate 3' end of probe I. Said probe I further comprising a primer binding section (PBS(I)), located 5' from the region Ir. Said probe I and/or II may contain a stuffer region and/or a ZipDectCode (ZDc or DET) also referred to herein as detector region (DET). For instance, said stuffer region and/or a DET on probe I may be located between region Ir or tss(I) and PBS(I).

The detector region (DET) comprises a unique sequence which can be used for identification of amplified products. The DET will hybridize to its complementary oligonucleotide detector probe (e.g. cDET) present during the amplification reaction. It should be noted that for all structures of ligated probes provided by the methods according to the invention, the ZDc (or DET) can be substituted by a complementary ZDc (cZDc or cDET) since upon amplification a double stranded nucleic acid will be formed from which at least one strand will comprise a ZDc (or DET) detectable by the oligonucleotide detector probe. DET and cDET refer to DNA segments used for real time detection during amplification, where cDET has the complementary sequence of DET.

The probe II comprises a region IIr or tss(II) specifically hybridising to a target region, said region IIr or tss(II) being located at the ultimate 5' end of probe II. Said probe II further comprising a primer binding section (PBS(II)), located 3' from the region IIr. Probe I or Probe II may further comprise an identifier region, such as a Zipcode (Zc or ZIP) or ZipComcode (ZCc or cZIP), located in-between the region Ir or tss(I) and PBS(I) or the region IIr or tss(II) and PBS(II), respectively. ZIP and cZIP refer to the DNA segments used for microarray detection, where cZIP has the complementary sequence of ZIP. The ZCc (or cZIP) or its complement the Zc (or ZIP) is a unique sequence for identification of the eventually amplified products. The ZCc (or cZIP) will hybridize to its complement the Zc (or ZIP). The complement of the amplified product is present on for instance a microchip (capture probe; see below). Upon hybridisation, the target region Ir of probe I (tss(I)) is located adjacent to the target region IIr of probe II (tss(II)). The ZCc (or cZIP) or Zc (or ZIP) and the PBSs are located at the ends of the probes, and are not capable of hybridizing to the target sequence. When both probes are hybridized to the target sequence, and are located adjacent to each other, the probes can be ligated using a ligase, such as for example Pfu DNA ligase. After ligation, the ligated probes may be amplified using at least one primer that is capable of hybridizing to a primer binding section. Preferably, amplification is carried out by PCR, using probe I with a PBS(I) which differ from probe II with PBS(II). Hence, primer I binding to the region characterized by PBS(I) will differ from primer II binding to the region characterized by PBS(II). It will be appreciated that if primer I comprises a sequence substantially complementary to PBS(I), then primer II comprises a sequence substantially identical to PBS(II), and vice versa, that if primer I comprises a sequence substantially identical to PBS(I), then primer II comprises a sequence substantially complementary to PBS(II).

In a further embodiment, Probe I or Probe II may comprise a Zipcode. Since it is the object of the present invention that upon ligation of Probe I and Probe II, the ligated probe is amplified, it can be understood that the amplified ligated probe should contain a ZipComcode for it to hybridise with the Zipcode, present on for instance a microchip. Therefore providing Probe I or Probe II with a Zipcode would also result in an amplified ligated probe comprising a ZipComcode.

One of the primers may be labelled, for example at its 5' end. Either the first primer or second primer may be labelled at its 5' end. Alternatively, both primers may be labelled with the same or different labels. In a multiplex, the method may operate using one common primer, e.g. hybridising to PBS(I), and one probe specific primer, e.g. hybridising to PBS(II). It will be appreciated that the common primer may hybridise to PBS(II), while the probe specific primer hybridises to PBS(I). In a further embodiment, probe I contains a label.

Hence, in the method according to the present invention said nucleic acid and/or cDNA may be amplified using the Ligase Detection Reaction, comprising a first nucleic acid probe complementary to a distinct part of said target nucleic acid and a second nucleic acid probe complementary to a second part of said target nucleic acid located essentially adjacent to said distinct part of said target nucleic acid, wherein said first nucleic acid probe further comprises a 5' located primer binding section and possibly a stuffer, and said first or said second nucleic acid probe comprises a 3' located ZipComcode tag which is essentially non-complementary to said target nucleic acid and a primer binding section, which in case of said second nucleic acid probe is located 3' from the ZipComcode. The method further comprising incubating said nucleic acid and/or cDNA allowing hybridisation of complementary nucleic acids, connecting any essentially adjacent probes (by ligating), and amplifying any connected probe nucleic acid, wherein amplification is initiated by binding of nucleic acid primers specific for primer binding sections.

Thus, the present invention relates to a method as described herein, wherein said connecting step comprises the use or activity of a ligase, such as T4 DNA ligase, T4 RNA ligase, *E. coli* DNA ligase, or a thermostable ligase such as Taq DNA ligase, Pfu DNA ligase, Tth DNA ligase or Ampligase™. Conditions under which a ligation reaction may occur are well known in the art.

A typical structure of ligated probes is the following:
I: 5'-PBS(I)-[stuffer]-target specific sequence I . . . target specific sequence II-[stuffer]-ZCc (or cZIP)-[stuffer]-PBS(II)-3',
II: 5'-PBS(I)-[stuffer]-ZCc (or cZIP)-[stuffer]-target specific sequence I . . . target specific sequence II-[stuffer]-PBS(II)-3',
III: 5'-PBS(I)-[stuffer]-ZCc (or cZIP)-[stuffer]-ZDc (or DET)-[stuffer]-target specific sequence I . . . target specific sequence II-[stuffer]-PBS(II)-3',
IV: 5'-PBS(I)-[stuffer]-ZDc (or DET)-[stuffer]-ZCc (or cZIP)-[stuffer]-target specific sequence I . . . target specific sequence II-[stuffer]-PBS(II)-3',
V: 5'-PBS(I)-[stuffer]-ZCc (or cZIP)-[stuffer]-target specific sequence I . . . target specific sequence II-[stuffer]-ZDc (or DET)-[stuffer]-PBS(II)-3',
VI: 5'-PBS(I)-[stuffer]-ZDc (or DET)-[stuffer]-target specific sequence I . . . target specific sequence II-[stuffer]-ZCc (or cZIP)-[stuffer]-PBS(II)-3',
VII: 5'-PBS(I)-[stuffer]-target specific sequence I . . . target specific sequence II-[stuffer]-ZDc (or DET)-[stuffer]-ZCc (or cZIP)-[stuffer]-PBS(II)-3', or
VIII: 5'-PBS(I)-[stuffer]-target specific sequence I . . . target specific sequence II-[stuffer]-ZCc (or cZIP)-[stuffer]-ZDc (or DET)-[stuffer]-PBS(II)-3'.
(the regions between square brackets are optional)

In the case that labelled primer I comprises a sequence substantially identical to PBS(I) and non-labelled primer II comprises a sequence substantially complementary to PBS(II), the typical structures of the ligated probe after amplification are:
I: 5'-Label-PBS(I)-[stuffer]-target specific sequence I . . . target specific sequence II-[stuffer]-ZCc (or cZIP)-[stuffer]-PBS(II)-3',
II: 5'-Label-PBS(I)-[stuffer]-ZCc (or cZIP)-[stuffer]-target specific sequence I . . . target specific sequence II-[stuffer]-PBS(II)-3',
III: 5'-Label-PBS(I)-[stuffer]-ZCc (or cZIP)-[stuffer]-ZDc (or DET)-[stuffer]-target specific sequence I . . . target specific sequence II-[stuffer]-PBS(II)-3', IV: 5'-Label-PBS(I)-[stuffer]-ZDc (or DET)-[stuffer]-ZCc (or cZIP)-[stuffer]-target specific sequence I . . . target specific sequence II-[stuffer]-PBS(II)-3', V: 5'-Label-PBS(I)-[stuffer]-ZDc (or cZIP)-[stuffer]-target specific sequence I . . . target specific sequence II-[stuffer]-ZDc (or DET)-[stuffer]-PBS(II)-3', VI: 5'-Label-PBS(I)-[stuffer]-ZDc (or DET)-[stuffer]-target specific sequence I . . . target specific sequence II-[stuffer]-ZCc (or cZIP)-[stuffer]-PBS(II)-3', VII: 5'-Label-PBS(I)-[stuffer]-target specific sequence I . . . target specific sequence II-[stuffer]-ZDc (or DET)-[stuffer]-ZCc (or cZIP)-[stuffer]-PBS(II)-3', or VIII: 5'-Label-PBS(I)-[stuffer]-target specific sequence I . . . target specific sequence II-[stuffer]-ZCc (or cZIP)-[stuffer]-ZDc (or DET)-[stuffer]-PBS(II)-3'.

(the regions between square brackets are optional)

In yet another embodiment, non-labelled primer I comprises a sequence substantially identical to PBS(I) and labelled primer II comprises a sequence substantially complementary to PBS(II). The typical structure of ligated probes is the following:

I: 5'-PBS(I)-[stuffer]-Zc (or ZIP)-[stuffer]-target specific sequence I . . . target specific sequence II-[stuffer]-PBS(II)-3', II: 5'-PBS(I)-[stuffer]-Zc (or ZIP)-[stuffer]-ZDc (or DET)-[stuffer]-target specific sequence I . . . target specific sequence II-[stuffer]-PBS(II)-3', III: 5'-PBS(I)-[stuffer]-ZDc (or DET)-[stuffer]-Zc (or ZIP)-[stuffer]-target specific sequence I . . . target specific sequence II-[stuffer]-PBS(II)-3', or IV: 5'-PBS(I)-[stuffer]-Zc (or ZIP)-[stuffer]-target specific sequence I . . . target specific sequence II-[stuffer]-ZDc (or DET)-[stuffer]-PBS(II)-3'.

(the regions between square brackets are optional)

And the typical structures of the ligated probe after amplification are:

I: 5'-Label-cPBS(II)-[stuffer]-complementary target specific sequence II (ctss II)—-complementary target specific sequence I (ctss I)-[stuffer]-ZCc (or cZIP)— cPBS(I)-3', II: 5'-Label-cPBS(II)-[stuffer]-ctss II . . . ctss 1-[stuffer]-cZDc (or cDET)-[stuffer]-ZCc (or cZIP)-[stuffer]-cPBS(I)-3', III: 5'-Label-cPBS(II)-[stuffer]-ctss II . . . ctss 1-[stuffer]-ZCc (or cZIP)-[stuffer]-cZDc (or cDET)-[stuffer]-cPBS(I)-3', IV: 5'-Label-cPBS(II)-[stuffer]-cZDc (or cDET)-[stuffer]-ctss II . . . ctss 1-[stuffer]-ZCc (or cZIP)-[stuffer]-cPBS(I)-3'.

It should be noted that in case a labelled primer II comprising a sequence substantially complementary to PBS(II) is used, the first and second nucleic acid probes should provide Zipcodes instead of ZipComcodes and preferably the Zipcode is positioned on the first nucleic acid probe. By providing the Zipcode on the first nucleic acid probe the labelled strand of the amplified ligated probe will contain a ZipComcode.

In a preferred embodiment of the present invention, the ZDc (or DET) is provided on the non-labelled strand of the amplified ligated probe.

Figure 2:
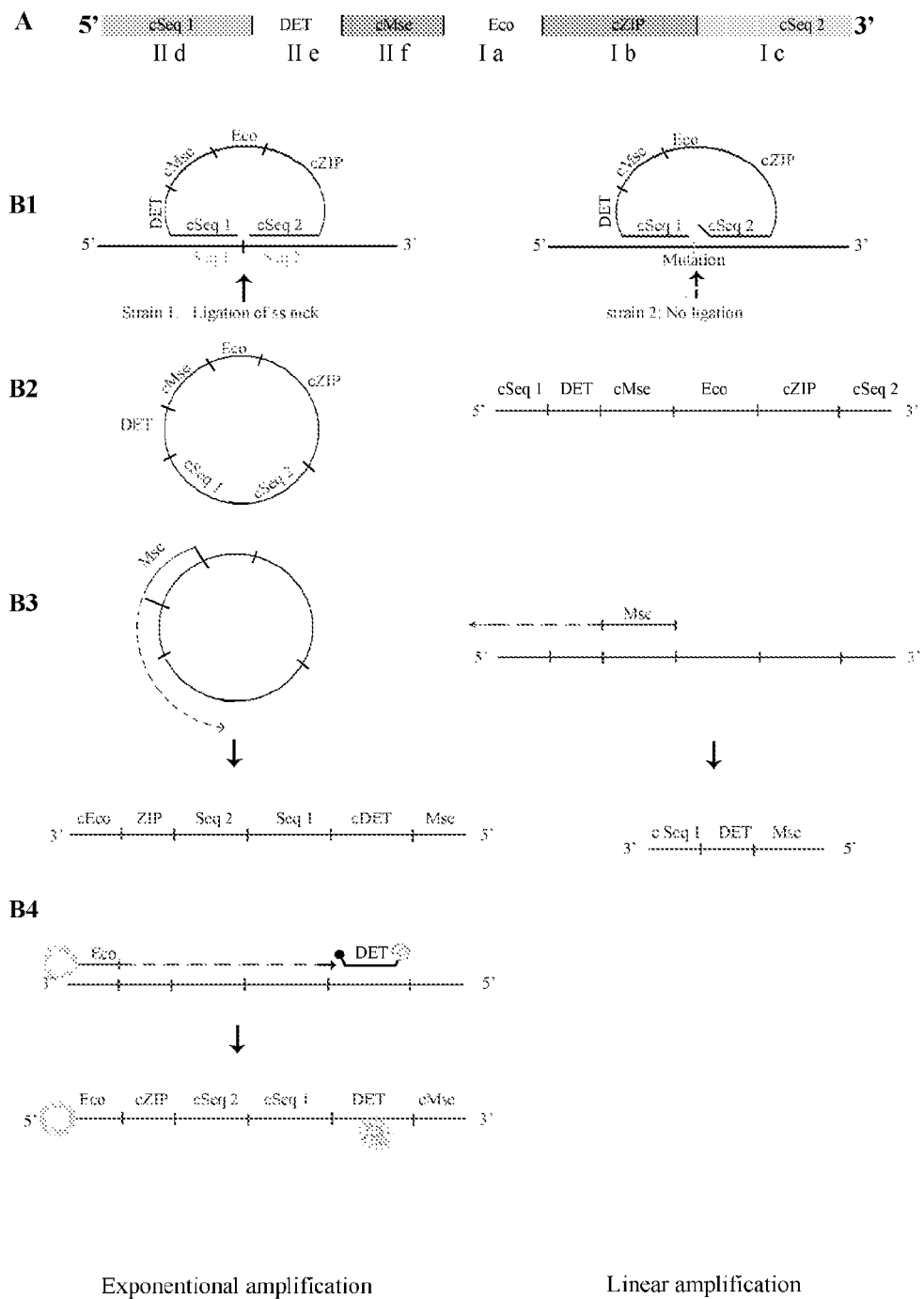

In a further embodiment, said first nucleic acid probe is coupled with its 5' end to the 3' end of said second nucleic acid probe, possibly via a stuffer region (FIG. 2).

It should be noted that in the instance that either a labelled primer I or a labelled primer II is used during the amplification of the ligated probe, a double stranded amplified ligated probe will be formed wherein one of the strands will be labelled, while the other strand will not be labelled. The present invention provides that the labelled strand of the amplified ligated probe comprises a ZipComcode, enabling this strand to hybridise with the Zipcode, present on for instance a microchip. Either the labelled or the non-labelled strand of the amplified ligated probe comprises a ZipDectcode, enabling this strand to be detected by the complementary oligonucleotide detector probe. By providing the ZCc (or cZIP) and the ZDc (or DET) on respectively the labelled and the non-labelled strand of the amplified ligated probe, the detection of both occurs separately from each other without any hindrance between both detection strategies. In first instance the detection of the ZDc (or DET) will provide information regarding the presence or absence of the amplified ligated probe and consequently the presence or absence of a contaminating micro-organism, whereas the samples that provide a positive detection signal of the ZDc (or DET) will subsequently be hybridized in the second screening step where the labelled strand of the amplified ligated probe containing the ZCc (or cZIP) will be detected.

In a preferred embodiment, primer I is labelled if the ZipComcode is located on the first or the second nucleic acid probe.

In an embodiment, the present invention relates to a method as described herein, wherein (see FIG. 5):

(a) said first nucleic acid probe comprises from 5' to 3': a Primer Binding Sequence I (PBS(I)), ZipComcode (ZCc or cZIP), and a target specific sequence I (tss(I)), said second nucleic acid probe comprises from 5' to 3': a target specific sequence II (tss(II)), ZipDectCode (ZDc or DET) and a Primer Binding Sequence II (PBS(II)), and preferably primer I is labelled;

(b) said first nucleic acid probe comprises from 5' to 3': a PBS(I), ZDc (or DET), and tss(I), said second nucleic acid probe comprises from 5' to 3': a tss(II), ZCc (or cZIP) and PBS(II), and preferably primer I is labelled;

(c) said first nucleic acid probe comprises from 5' to 3': a PBS(I), complementary ZDc (cZDc or cDET) and tss(I), said second nucleic acid probe comprises from 5' to 3': a tss(II), ZCc (or cZIP) and PBS(II), and preferably primer I is labelled;

(d) said first nucleic acid probe comprises from 5' to 3': a PBS(I), ZCc (or cZIP), ZDc (or DET) and tss(I), said second nucleic acid probe comprises from 5' to 3': a tss(II) and PBS(II), and preferably primer I is labelled;

(e) said first nucleic acid probe comprises from 5' to 3': a PBS(I), ZCc (or cZIP), cZDc (or cDET), and tss(I), said second nucleic acid probe comprises from 5' to 3': a tss(II) and PBS(II), and preferably primer I is labelled;

(f) said first nucleic acid probe comprises from 5' to 3': a PBS(I), ZDc (or DET), ZCc (or cZIP) and tss(I), said second nucleic acid probe comprises from 5' to 3': a tss(II) and PBS(II), and preferably primer I is labelled;

(g) said first nucleic acid probe comprises from 5' to 3': a PBS(I), cZDc (or cDET), ZCc (or cZIP) and tss(I), and said second nucleic acid probe comprises from 5' to 3': a tss(II) and PBS(II), and preferably primer I is labelled;

(h) said first nucleic acid probe comprises from 5' to 3': a PBS(I) and tss(I), said second nucleic acid probe comprises from 5' to 3': a tss(II), ZDc (or DET), ZCc (or cZIP) and PBS(II), and preferably primer I is labelled;

(i) said first nucleic acid probe comprises from 5' to 3': a PBS(I) and tss(I), said second nucleic acid probe comprises from 5' to 3': a tss(II), ZCc (or cZIP), ZDc (or DET) and PBS(II), and preferably primer I is labelled;

(j) said first nucleic acid probe comprises from 5' to 3': a PBS(I), Zc (or ZIP) and tss(I), and said second nucleic acid probe comprises from 5' to 3': a tss(II), ZDc (or DET) and PBS(II), and preferably primer II is labelled;

(k) said first nucleic acid probe comprises from 5' to 3': a PBS(I), ZCc (or cZIP), ZDc (or DET) and tss(I), said second nucleic acid probe comprises from 5' to 3': a tss(II) and PBS(II), and preferably primer II is labelled,
(l) said first nucleic acid probe comprises from 5' to 3': a PBS(I), Zc (or ZIP), cZDc (or cDET) and tss(I), and said second nucleic acid probe comprises from 5' to 3': a tss(II) and PBS(II), and preferably primer II is labelled;
(m) said first nucleic acid probe comprises from 5' to 3': a PBS(I), ZDc (or DET), Zc (or ZIP) and tss(I), said second nucleic acid probe comprises from 5' to 3': a tss(II) and PBS(II), and preferably primer II is labelled; and/or,
(n) said first nucleic acid probe comprises from 5' to 3': a PBS(I), cZDc (or cDET), Zc (or ZIP) and tss(I), and said second nucleic acid probe comprises: a tss(II) and PBS(II), and preferably primer II is labelled.

Eco and Mse refer to the primer binding regions 1 and 2, cEco and cMse to their respective complementary sequences. ZIP and cZIP refer to the DNA segments used for microarray detection, where cZIP has the complementary sequence of ZIP. DET and cDET refer to DNA segments used for real time detection during amplification, where cDET has the complementary sequence of DET. cSeq-1 and cSeq-2 refer to DNA segments complementary to the target DNA.

In this regard, the person skilled in the art will appreciate that equivalent terms are used interchangeably in the present description, such as, cSeq-1 and cSeq-2 relate to target-specific sequence I and target-specific sequence II, respectively.

Eco and cMse relate to primer binding section I and primer binding section II, respectively. In a double-stranded PCR product, one strand will always have the sense sequence (Eco or Mse) of one primer, and the antisense or complementary sequence (cEco or cMse) of the other primer. So either Eco and cMse or cEco and Mse.

cZIP relates to ZipComcode, while ZIP relates to Zipcode
DET relates to ZipDectCode, while cDET relates to complementary ZipDectCode.

Also, the present invention relates to a method as described herein, wherein said probe I and/or probe II comprises a stuffer region. In this regard, a stuffer region is intended to part structural regions, such as the PBS, the ZCc (or cZIP), the Ir (tss(I)) or IIr (tss(II)), thereby avoiding or minimizing steric hindrance.

As already set out above, it will be appreciated that the label may be attached to at least one of the primers and/or probes, or in the alternative, may be incorporated during amplification. The label is for instance a fluorescent label. Accordingly, the present invention relates to a method as described herein, wherein at least one primer contains a label, and preferably a fluorescent label. This provides a cost efficient detection method.

It will be appreciated that RNA-DNA hybrids can act as substrates for T4 DNA ligase, as described by Charani Ranasinghe and Andrew A. Hobbs Affiliations in Elsevier Trends Journals Technical Tips Online, [Tip]01519 "A simple method to obtain the 5' ends of mRNA sequences by direct ligation of cDNA-RNA hybrids to a plasmid vector", which is incorporated herein by reference.

In the alternative, a probe or primer contains an RNA polymerase binding site. The ligated probes are subsequently amplified by the activity of an RNA polymerase, e.g. T4-, T7- or SP6 RNA polymerase.

The present invention especially contemplates that during the amplification procedure one or more detector molecules are present. The presence of detector molecules during the amplification enables the detection of the accumulation of amplified target nucleic acids and therefore this step provides a first screening of the samples. Since a large amount of the samples are presumed to be negative, the first fast and cheap screening step assesses whether or not contaminating microorganisms are present or absent in the sample. Therefore, the more complicated, time consuming and more expensive second screening step can be avoided when no micro-organisms are present.

The amplification of the target nucleic acids can be detected and/or quantified using the fluorescence or phosphorescence of a dye, which fluorescence or phosphorescence is associated either directly or indirectly with the multiplication of the amplified DNA. Since the amplification of the target nucleic acids is detected using detector molecules which can either be dyes intercalating double-stranded DNA or oligonucleotide detector probes complementary to the target nucleic acids, a person skilled in the art would expect these detector molecules to disrupt the hybridization reaction of the second screening step if these detector molecules are present during the hybridization. Since the hybridization of DNA is a very delicate process influenced by a large variety of environmental factors, the presence of these detector molecules during the hybridization reaction should be avoided. Removing these detector molecules prior to the second screening step is an elaborate process. However, the inventors have surprisingly found that the presence of these detector molecules during the second screening step does not disrupt the results obtained during this screening nor do they increase the number of false positive or false negative results.

A direct detection method can for instance use a dye which binds nonspecifically to double-stranded DNA and only fluoresces or phosphoresces in connection with this binding. When the target nucleic acids are amplified, said dye binds to the newly formed double-stranded DNA such that the measurable fluorescence or phosphorescence increases. Examples of such dyes include, but are not limited to, SYBR Green-I®, ethidium bromide, propidium iodide, TOTO®-1{Quinolinium, 1-1'-[1,3-propanediylbis[(dimethyliminio)-3,1-propanediyl]]bis[4-[(3-methyl-2(3H)-benzothiaz-olylidene) methyl]]-, tetraiodide}, and YoPro® {Quinolinium,4-[(3-methyl-2(3H)-benzoxazolylidene) methyl]-1-[3-(trimethylammonio)propyl]-, diiodide}. Most preferred dye for the instant invention is a non-asymmetrical cyanide dye such as SYBR Green-I®, manufactured by Molecular Probes, Inc. (Eugene, Oreg.).

Another direct detection method that can be used in the method of the present invention is a method using oligonucleotide detector probes. Oligonucleotide detector probes are short oligonucleotides complementary to the target nucleic acids. These oligonucleotide detector probes provide a fluorescent signal upon binding with the amplified target nucleic acids. The method by which the fluorescent or phosphorescent signal is provided by the oligonucleotide detector probes can be any method known in the art.

In a specific embodiment of the present invention, the oligonucleotide detector probes are provided with the fluorescence resonance energy transfer (FRET) technique. The FRET oligonucleotide detector probe comprises of two fluorescent dyes, i.e. a "reporter" at one, for instance 5', end, and a "quencher" at the other, for instance 3', end, of the FRET oligonucleotide detector probe. In the FRET oligonucleotide detector probes, the dyes are held, in the unbound state, in spatial proximity by means of a loop arrangement (hairpin loop). The hairpin loop is generated by means of complementary sequences which are present at the ends of the actual probe sequence. Because of its proximity to the reporter, the quencher dye is able to quench its fluorescence by means of the FRET. Upon binding with the amplified target nucleic acids, the FRET oligonucleotide detector probe which is complementary to the target nucleic acid sequence disrupts the hairpin loop and thereby separates the two dyes, resulting in the FRET interference being abolished and the fluorescence of the reporter dye becoming measurable.

In another specific embodiment of the present invention a FRET oligonucleotide detector probe is provided which, in contrast to the abovementioned probes, does not possess any hairpin loop. During the amplification step, the exonuclease activity of the polymerase enzyme which is replicating the target nucleic acids, degrades the FRET probe, which is bound to the target nucleic acid, at its 5' end such that the reporter dye is released from the probe. As a result, the reporter dye is no longer in the spatial vicinity of the quencher dye which means that its fluorescence is no longer quenched and can now be measured. The amplification of the target DNA, and, as a result, the increase in the release of the reporter dye, can then be detected using a suitable optical measuring system.

Molecules that are frequently used as tags for FRET include fluorescein, 5-carboxyfluorescein (FAM), 2'7-dimethoxy-4'57-dichloro-6-carboxyfluorescein (JOE), rhodamine, 6-carboxyrhodamine (R6G), N,N,N7,N'-tetramethyl-6-carboxyrhodamine (TAMRA), 6-carboxy-X-rhodamine (ROX), 4-(4'-dimethylaminophenylazo)benzoic acid (DABCYL), and 5-(2'-aminoethyl)aminonaphthalene-1-sulfonic acid (EDANS). Other potential FRET donor or acceptor molecules are known in the art (See U.S. Pat. No. 5,866,336, Table 1). The skilled artisan will be familiar with the selection of pairs of tag molecules for FRET (U.S. Pat. No. 5,866,336).

Different oligonucleotide detector probes may be used for carrying out the method of the present invention including, but not limited to a 5' nuclease assay in which the oligonucleotide detector probe carries a fluorogenic reporter dye at its 5' end and a quencher at its 3' end, Scorpion primers in which a primer is covalently linked to the probe, the primer probe complex comprising a fluorophore and a quencher molecule each linked to either the primer or the probe, and Molecular Beacons which are hairpin shaped molecules with an internally quenched fluorophore.

In a 5' nuclease assay the oligonucleotide detector probe such as for instance a Taqman probe carries a fluorogenic reporter dye at its 5' end and a quencher at its 3' end. When the probe is intact, the reporter dye emission is quenched. During each cycle of PCR, the DNA polymerase cleaves the reporter dye from the probe. Once separated from the quencher, the reporter dye emits its characteristic fluorescence. FIG. 6a provides as schematic representation of the real time amplification reaction using TaqMan probes for real time detection. Eco and Mse refer to the primer binding regions 1 and 2, cEco and cMse to their respective complementary sequences. ZIP and cZIP refer to the DNA segments used for microarray detection, where cZIP has the complementary sequence of ZIP. DET and cDET refer to DNA segments used for real time detection during amplification, where cDET has the complementary sequence of DET. cSeq-1 and cSeq-2 refer to DNA segments complementary to the target DNA. "1. Annealing" displays the probe pairs hybridized to the target DNA; "2. Ligation" displays the connected probe pairs as a result of the ligation reaction; "3. Cycle 1" displays the double-stranded structure that results from copying of the connected probe pairs through extension of the Mse primer by the DNA polymerase; "4. Cycle n" displays the Eco-primer and TaqMan probe hybridized to one of the strands of the PCR product. A fluorescent signal is generated when the DNA polymerase extends into the TaqMan probe and releases the fluorescent label from the TaqMan probe.

Scorpion primers comprise a primer that is linked to the oligonucleotide detector probe. This probe both carries a fluorophore and a quencher, which may be on the same DNA strand or on a complementary DNA strand. In the absence of the target sequence, the quencher nearly absorbs the fluorescence emitted by the fluorophore. During the PCR reaction, in the presence of the target, the fluorophore and the quencher separate which leads to an increase in the fluorescence emitted. The fluorescence can be detected and measured in the reaction tube. FIG. 6b provides a schematic representation of the real time amplification reaction using Scorpion probes for real time detection. Eco and Mse refer to the primer binding regions 1 and 2, cEco and cMse to their respective complementary sequences. ZIP and cZIP refer to the DNA segments used for microarray detection, where cZIP has the complementary sequence of ZIP. DET and cDET refer to DNA segments used for real time detection during amplification, where cDET has the complementary sequence of DET. cSeq-1 and cSeq-2 refer to DNA segments complementary to the target DNA. "1. Annealing" displays the probe pairs hybridized to the target DNA; "2. Ligation" displays the connected probe pairs as a result of the ligation reaction; "3. Cycle 1" displays the double-stranded structure that results from copying of the connected probe pairs through extension of the Mse primer by the DNA polymerase; "4. Cycle 2" displays the double-stranded extension product from the Scorpion primer. After denaturation one of the strands refolds (Scorpion reaction) to generate the Scorpion structure emitting the fluorescent signal.

Molecular beacons refers to a method where the oligonucleotide hybridization probes are hairpin shaped molecules with an internally quenched fluorophore. Upon presence of the target sequence the hairpin is removed and the fluorophore is no longer quenched. FIG. 6c provides a schematic representation of the real time amplification reaction using Molecular Beacons for real time detection. Eco and Mse refer to the primer binding regions 1 and 2, cEco and cMse to their respective complementary sequences. ZIP and cZIP refer to the DNA segments used for microarray detection, where cZIP has the complementary sequence of ZIP. DET and cDET refer to DNA segments used for real time detection during amplification, where cDET has the complementary sequence of DET. cSeq-1 and cSeq-2 refer to DNA segments complementary to the target DNA. "1. Annealing" displays the probe pairs hybridized to the target DNA; "2. Ligation" displays the connected probe pairs as a result of the ligation reaction; "3. Cycle 1" displays the double-stranded structure that results from copying of the connected probe pairs through extension of the Mse primer by the DNA polymerase. Denaturation of the extension product of the Mse primer and subsequent reannealing with the Molecular Beacon changes the conformation of the Molecular Beacon separating the fluorophor from the quencher thereby emitting the fluorescent signal.

Besides enabling the real time detection of the amplified target nucleic acids the use of FRET oligonucleotide detector probes also enables the quantification of the target nucleic acids.

It will be apparent that the present invention relates to a method as described herein, wherein a signal is detected after and/or during amplification of the target nucleic acids. The said signal is preferably a fluorescent or phosphorescent signal, and said fluorescent or phosphorescent signal may be detected by a CCD camera or by laser scanning.

By providing detector molecules during the amplification procedure it is possible to perform in the first step of the method of the present invention a screening towards the presence of contaminating micro-organisms in the samples. Since the second step of the method of the invention, which involves the further characterization and identification of the contaminating micro-organisms by hybridizing the amplified target nucleic acids on a microarray, has a larger cost per test, a reduction of the samples to be analyzed in the second step of the method of the present invention would be highly beneficial.

Therefore, the present invention provides a method wherein the amplified target nucleic acids hybridized in step (d) are the target sequences providing a positive signal in step (c) of the method of the present invention.

In a specific embodiment of the present invention, said detector molecules are one or more oligonucleotide detector probes and more preferably FRET oligonucleotide detector probes, having a sequence at least partially complementary to a target nucleic acid sequence to be detected and including a fluorescent reporter molecule and a fluorescent quencher molecule capable of quenching the fluorescence of said reporter molecule, said oligonucleotide probe existing in at least one single-stranded, partially single-stranded or double-stranded conformation when unhybridized where said quencher molecule quenches the fluorescence of said reporter molecule, said oligonucleotide probe existing in at least one conformation when hybridized to said target nucleic acid where the fluorescence of said reporter molecule is unquenched.

In a more specific embodiment of the present invention, the sequence of said oligonucleotide detector probes is at least complementary to at least one region, e.g. ZCc (or cZIP) or Zc (or ZIP) of the first nucleic acid probe and/or at least one region, e.g. ZCc (or cZIP) or Zc (or ZIP), of the second nucleic acid probe.

The present invention provides that at least two oligonucleotide detector probes are provided with different fluorescent reporter molecules thereby providing an assay where depending on the detected type of fluorescent reporter molecule or the detected amount of each fluorescent reporter molecule information is obtained regarding the type of micro-organism that is detected as well as the amount of each type of micro-organism.

In a further embodiment of the present invention the first nucleic acid probe and/or the second nucleic acid probe further comprise at least one ZipDectCode (ZDc or DET), which is (i) essentially complementary (for instance after amplification) to one or more oligonucleotide detector probes used for detecting the accumulation of the reaction products during the amplification reaction of step (b5), (ii) essentially non-complementary to said target nucleic acid and (iii) which is located in between the target sequence and the primer binding section.

Said ZipDectCode (ZDc or DET) is a unique sequence for identification of the eventually amplified products. The ZDc (or DET) will hybridize to its complementary oligonucleotide detector probe present during the amplification reaction. Consequently, when oligonucleotide detector probes are used for the detection of the amplified target nucleic acids, said oligonucleotide detector probe would comprise a complementary ZipDectCode (cZDc or cDET), an oligonucleotide sequence complementary with the ZDc (DET).

In a specific embodiment of the present invention, the method is provided in such a way that the entire screening process is performed in a closed system. To avoid contamination and provide highly reliable results the method of the present invention should be performed in an automated manner and in a closed system thereby reducing the risks for contamination and user errors.

Genetic markers represent (mark the location of) specific loci in the genome of a species or closely related species. A sampling of different genotypes at these marker loci reveals genetic variation. The genetic variation at marker loci can then be described and applied to diagnostics and the like. Genetic variation between species may be ascribed to single nucleotide substitutions in the DNA or the 16S, 18S, 23S and/or 28S rRNA. The target binding region of the probes may be adapted correspondingly. For example, a set of four probes I may be provided, each of which comprising a different 3' ultimate nucleotide, e.g. probe I-A, probe I-C, probe I-G and probe I-T, containing the nucleotide A, C, G and T respectively at its 3' end. It will then be advantageous if the PBS of each probe I, is specific and corresponds to said ultimate nucleotide. In other words, the PBS of each probe I hybridises to a different primer I. Hence, the present invention contemplates probe I-A with PBS(I-A), which hybridises to the corresponding primer I-A, probe I-C with PBS(I-C), which hybridises to the corresponding primer I-C, probe I-G with PBS(I-G), which hybridises to the corresponding primer I-G, and probe I-T with PBS(I-T), which hybridises to the corresponding primer I-T. Each of said primers I-A, I-C, I-G and I-T may comprise a different label. It will be appreciated by the person skilled in the art that variations on this theme are conceivable, e.g. where the genetic marker is located within the target region of the probes, or on the ultimate 5' end of probe II. In the case that the genetic marker is located in probe II, the PBS(II) may be adapted as described above for probe I. Furthermore, the PBS, i.e. PBS(I) and PBS(II) may be identical or different. Accordingly, the present invention relates to a method as described herein, wherein probe I, i.e. said first nucleic acid probe, and/or probe II, i.e. said second nucleic acid probe, specifically hybridises to a genetic marker. Also, the present invention relates to a method as described herein, wherein 4 variants of probe I, i.e. said first nucleic acid probe, are provided, said 4 variants being substantially identical, except that each of the 4 variants containing a different nucleotide at its ultimate 3' end. In addition, the present invention relates to a method as described herein, wherein each of said 4 variants containing a different primer binding section I.

In a further embodiment, the present invention relates to a method as described herein, wherein at least two groups of pairs of first and second nucleic acid probes are provided, wherein each group of first and second nucleic acid probes hybridises to a specific target nucleic acid, and comprises a specific primer binding site I and/or II. In a preferred embodiment each group of first and second nucleic acid probes have identical primer binding site I and/or II. In a further aspect, the invention relates to a method as described herein, wherein at least two groups of pairs of first and second nucleic acid probes are provided, wherein each group of first and second nucleic acid probes hybridises to a specific target nucleic acid, and the first nucleic acid probe of each group comprises a specific identifier region, preferably a ZipComcode or Zipcode. As such, the identifier region, such as a ZCc (or cZIP) or Zc (or ZIP) may be located on the nucleic acid probe in between the target-specific sequence and the primer binding sequence. In a further aspect, the first nucleic acid probe is attached or coupled with its 5' end to the 3' end of said second nucleic acid probe, possibly via a stuffer region. It will be understood that a circular probe results after ligating target-specific sequence I to target-specific sequence II.

Accordingly, the present invention relates to a method as described herein, wherein each of the primers binding to each of the different primer binding section I of said 4 variants contains a different fluorescent label.

Accordingly, the present invention relates to a method as described herein, wherein a set of two adjacent probes is provided for the micro-organisms as defined supra. Also, these probes may be coupled.

The method described herein relates to the simultaneous detection of various contaminating micro-organisms, by providing at least one set, and preferably more than one set of two probes, specifically designed to identify and/or characterise the presence of a contaminating micro-organism (multiplex). The different sets of probes should preferably not cross-hybridise, while on the other hand the melting temperature Tm of the different sets of probe/primers is about similar, e.g. all between 60 and 70° C. Commonly available computer programmes, such as Probe Match, Michigan State University, East Lansing, Mich. USA, Oligo 5.0 software (PE Biosystems, Foster City, Calif., USA), and using Clustal W Algorithm, may facilitate the design of specific probes. Preferably, the primers/probes have a melting temperature Tm between about 37-85° C., or 50-80° C., or 55-75° C., or 60-70° C. As such, the present invention relates also to multiplex amplification.

In another aspect, the present invention relates to a method as described herein, comprising providing at least one set of two primers, wherein the first primer (primer A) comprises a 5' located label and a region A specifically hybridising to a first target nucleic acid region, said region A being located at the ultimate 3' end of primer A, and wherein the second primer (primer B) comprises a 3' located ZipComcode and a region B specifically hybridising to a second target nucleic acid region, said region B being located at the ultimate 5' end of primer B; the first target nucleic acid region target region being located 3' adjacent to the second target nucleic acid region; incubating said target nucleic acid with said primer A and said primer B under conditions allowing hybridisation of complementary nucleic acids; connecting any essentially adjacent primers; and hybridising the connected primers to a capture probe, which comprises a region essentially complementary to the ZipComcode, and which is present on a flow-through microarray. As such, said primer A may specifically hybridise to a genetic marker. In a further aspect, 4 variants of primer A are provided, said 4 variants being substantially identical, except that each of the 4 variants contain a different nucleotide at its ultimate 3' end, and each of the 4 variants contain a different fluorescent label.

After collecting the contaminating micro-organism, isolation of its nucleic acid and amplification, the amplified nucleic acids or amplified nucleic acid mixture may be analysed. A convenient method to analyse said amplified nucleic acid or said amplified nucleic acid mixture is by determining the sequence thereof. Techniques to determine the sequence of nucleic acids are well known in the art. Accordingly, the present invention relates to a method as described herein, wherein the analysis comprises determining the sequence of the amplified nucleic acid mixture. Said sequence may be determined via enzymatic, chemical or physical means. The sequence determined of the contaminating organism may be compared with sequences stored in a databank. Also the step of analysing in the method for characterising micro-organisms possibly present in a sample according to the present invention, may comprise providing a computer readable medium carrying computer output data having a database characterising micro-organisms based on nucleotide sequences, providing a computer and algorithm, processing the computer output data to determine the micro-organism.

Another convenient method to characterise the contaminating micro-organisms is by performing an amplified fragment-length polymorphism analysis (AFLP), ribotyping, Multiple Loci VNTR Analysis (MLVA), REP-PCR, RFLP, Pulsed field gel electrophoresis or other fingerprinting techniques known in the art.

Another embodiment of the present invention relates to the use of arrays, e.g. microarrays, for the analysis of the amplified nucleic acids. Arrays may contain thousands of DNA spots. A single array has the potential for a broad identification capacity, i.e. many different contaminating micro-organisms may be analysed on one microarray, in one go. In addition, the method of the invention does not require laborious cross-hybridisations and may provide an open database of hybridisation profiles, avoiding the limitations of traditional DNA-DNA hybridisations.

In the presence of a perfectly matching template, the probes may be ligated by the action of a DNA ligase. After ligation, said probes may be amplified. Next, the ligated probes, which may be or may be not amplified, are brought into contact with a capture probe, under hybridizing conditions. Hybridizing conditions are well known in the art, or may be determined without difficulty by the person skilled in the art, see e.g. "Molecular Cloning: A Laboratory Manual" Second Edition (Sambrook et al., 1989) and "Current Protocols in Molecular Biology" (F. M. Ausubel et al., eds., 1987, and periodic updates). Said capture probe comprises a complementary sequence relative to the target nucleic acid sequence, or a part thereof, such as the ZCc (or cZIP). The capture probes may be located on a microarray. Hence, the microarray comprises the complementary sequences of the target nucleic acid sequences, i.e. the capture probe. The location of the capture probe on the microarray is known.

Hence, the present invention relates to a method as described herein, wherein said analysing comprises hybridising the amplified nucleic acids or said amplified nucleic acid mixture to a capture probe, said capture probe hybridising specifically to said amplified nucleic acids or said amplified nucleic acid mixture. The term "hybridising specifically" relates to a perfect match between a region of the analyte, e.g. the ZCc (or cZIP) of the amplified product, and the capture probe on the microarray. Hybridising specifically takes the length, G/C content and hybridisation conditions, such as salt and temperature, into account as known by the person skilled in the art. Accordingly, the present invention relates to a method as described herein, wherein said capture probe is located on a microarray. The capture probe is spatially addressable on the microarray.

The microarrays of the present invention may be of any desired size, from two spots to $10^6$ spots or even more. The upper and lower limits on the size of the substrate are determined solely by the practical considerations of working with extremely small or large substrates.

For a given substrate size, the upper limit is determined only by the ability to create and detect the spots in the microarray. The preferred number of spots on a microarray generally depends on the particular use to which the microarray is to be put. For example, sequencing by hybridisation will generally require large arrays, while mutation detection may require only a small array. In general, microarrays contain from 2 to about $10^6$ spots, or from about 4 to about $10^5$ spots, or from about 8 to about $10^4$ spots, or between about 10 and about 2000 spots, or from about 20 to about 200 spots.

Furthermore, not all spots on the microarray need to be unique. Indeed, in many applications, redundancies in the spots are desirable for the purposes of acting as internal controls (see e.g. FIG. 4).

A variety of techniques have been described for synthesizing and/or immobilizing arrays of polynucleotides, including in situ synthesis, where the polynucleotides are synthesized directly on the surface of the substrate (see, e.g., U.S. Pat. No. 5,744,305 to Fodor, et al.) and attachment of pre-synthesized polynucleotides to the surface of a substrate at discrete locations (see, e.g., WO 98/31836). Additional methods are described in WO 98/31836 at pages 41-45 and 47-48, among other places. The present invention is suitable for use with any of these currently available, or later developed, techniques.

Immobilization of pre-synthesized polynucleotides at different spatial addresses yields an array of polynucleotides whose sequences are identifiable by their spatial addresses.

In embodiments involving in situ synthesis of polynucleotides, the polynucleotides are synthesized in their usual manner. The synthetic scheme yields an array of polynucleotides whose sequences are identifiable by their spatial addresses.

The nature and geometry of the solid substrate will depend upon a variety of factors, including, among others, the type of array (e.g., one-dimensional, two-dimensional or three-dimensional) and the mode of attachment (e.g., covalent or non-covalent). Generally, the substrate can be composed of any material which will permit immobilization of the capture probe, e.g. polynucleotide, and which will not melt or otherwise substantially degrade under the conditions used to bind the capture probe, e.g. hybridise and/or denature nucleic acids. In addition, where covalent immobilization is contemplated, the substrate should be activated with reactive groups capable of forming a covalent bond with the capture probe to be immobilized.

Other exemplary suitable materials for use as substrates in the present invention include metal oxides. Metal oxides provide a substrate having both a high channel density and a high porosity, allowing high density arrays comprising different first binding substances per unit of the surface for sample application. In addition, metal oxides are highly transparent for visible light. Metal oxides are relatively cheap substrates that do not require the use of any typical microfabrication technology and, that offers an improved control over the liquid distribution over the surface of the substrate, such as electrochemically manufactured metal oxide membrane. Metal oxide membranes having through-going, oriented channels can be manufactured through electrochemical etching of a metal sheet. Metal oxides considered are, among others, oxides of tantalum, titanium, and aluminium, as well as alloys of two or more metal oxides and doped metal oxides and alloys containing metal oxides. The metal oxide membranes are transparent, especially if wet, which allows for assays using various optical techniques. Such membranes have oriented through-going channels with well controlled diameter and useful chemical surface properties. Patent application EP-A-0 975 427 is exemplary in this respect, and is specifically incorporated in the present invention. Accordingly, the present invention relates to a method as described herein, wherein said microarray is a flow-through microarray. Also, the present invention relates to a method as described herein, wherein said substrate is a porous substrate, said substrate may be an electrochemically manufactured metal oxide membrane. Preferably, said substrate comprises aluminium oxide. Accordingly, the present invention relates to a method as described herein, wherein said microarray is a PamChip®.

The composition of the immobilized capture probes is not critical. The only requirement is that they be capable of hybridising to a target nucleic acid of complementary sequence, e.g. the amplified nucleic acid, if any. For example, the capture probes may be composed of all natural or all synthetic nucleotide bases, or a combination of both. Non-limiting examples of modified bases suitable for use with the instant invention are described, for example, in Practical Handbook of Biochemistry and Molecular Biology, G. Fasman, Ed., CRC Press, 1989, pp. 385-392. While in most instances the polynucleotides will be composed entirely of the natural bases (A, C, G, T or U), in certain circumstances the use of synthetic bases may be preferred.

Moreover, while the backbones of the capture probes will typically be composed entirely of "native" phosphodiester linkages, they may contain one or more modified linkages, such as one or more phosphorothioate, phosphoramidite or other modified linkages. As a specific example, one or more immobilized polynucleotides may be a peptide nucleic acid (PNA), which contains amide interlinkages. Additional examples of modified bases and backbones that can be used in conjunction with the invention, as well as methods for their synthesis can be found, for example, in Uhlman & Peyman, 1990, Chemical Review 90(4):544-584; Goodchild, 1990, Bioconjugate Chem. 1(3):165-186; Egholm et al., 1992, J. Am. Chem. Soc. 114:1895-1897; Gryaznov et al., J. Am. Chem. Soc. 116:3143-3144, as well as the references cited in all of the above.

As such, the capture probes may include polymers of ribonucleotides and deoxyribonucleotides, with the ribonucleotide and/or deoxy-ribonucleotides being connected together via 5' to 3' linkages. The capture probes of the invention may be ribonucleic acids, for example sense or antisense ribonucleic acids, full-length or partial fragments of cRNA, full-length or partial fragments of mRNA, and/or ribo-oligonucleotides. Alternatively, capture probes of the invention may be deoxy-ribonucleic acids, preferably single-stranded full-length or fragments of sequences encoding the corresponding mRNAs. The form of the capture probes should be chosen so that they are complimentary to and form appropriate Watson-Crick hydrogen bonds with the amplified target nucleic acid and/or ligated probes in a sample.

As mentioned above, the capture probes may be polymers of synthetic nucleotide analogs. Such capture probes may be utilised in certain embodiments because of their superior stability under assay conditions. Modifications in the native structure, including alterations in the backbone, sugars or heterocyclic bases, have been shown to increase intracellular stability and binding affinity. Among useful changes in the backbone chemistry are phosphorothioates; phosphorodithioates, where both of the non-bridging oxygens are substituted with sulfur; phosphoroamidites; alkyl phosphotriesters and boranophosphates. A-chiral phosphate derivatives include 3'-O-5'-S-phosphorothioate, 3'-S-5'-O-phosphorothioate, 3'-$CH_2$-5'-O-phosphonate and 3'-NH-5-O-phosphoroamidate. Peptide nucleic acids replace the entire ribose phosphodiester backbone with a peptide linkage. Locked nucleic acids give additional conformational stability of sugar moiety due to additional bonds between 2'-carboxyl and 5' carboxyl or 4'-carboxyl groups of deoxyribose. Sugar modifications are also used to enhance stability and affinity. The a-anomer of deoxyribose may be used, where the base is inverted with respect to the natural p-anomer. The 2'-OH of the ribose sugar may be altered to form 2'-O-methyl or 2'-O-allyl sugars, which provides resistance to degradation without comprising affinity. Modification of the heterocyclic bases that find use in the method of the invention are those capable of appropriate base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Examples of non-naturally occurring bases that are capable of forming base-pairing relationships include, but are not limited to, aza- and deaza-pyrimidine analogues, aza- and deaza-purine analogues, and other heterocyclic base analogues, wherein one or more of the carbon and nitrogen atoms of the purine and pyrimidine rings have been substituted by heteroatoms, e.g., oxygen, sulfur, selenium, phosphorus, and the like. Examples of suitable non-naturally occurring bases include but are not limited to 8-oxo-guanine, and 8-oxo-adenine, 8-bromo-guanine, guanosine, xanthosine, wyosine, pseudouridine, 6-mercapto-guanine, 8-mercaptoguanine, 2-thioxanthine, 6-thioxanthine, 6-mercaptopurine, 2-amino-6-carboxymethyl-mercaptopurine, 2-mercaptopurine, 6-methoxypurine, 2-acetylamino-6-hydroxypurine, 6-methylthio-2-hydroxypurine, 2-dimethylamino-6-hydroxypurine, 2-hydroxy-purine, 2-aminopurine, 6-amino-2-dimethylallyl-purine, 2-thioadenine, 8-hydroxy-adenine, 8-methoxyadenine.

The immobilized capture probes may be as few as four, or as many as hundreds, or even more, nucleotides in length. Contemplated as capture probes according to the invention are nucleic acids that are typically referred to in the art as oligonucleotides and also those referred to as nucleic acids. Thus, the arrays of the present invention are useful not only in applications where amplified target nucleic acids or ligated probes are hybridised to immobilized arrays of relatively short (such as, for example, having a length of approximately 6, 8, 10, 20, 40, 60, 80, or 100 nucleotides) capture probes, but also in applications where relatively short capture probes are hybridised to arrays of immobilized target nucleic acids. The capture probes of the array can be of any desired sequence.

In a further embodiment, the microarray of the invention comprises a capture probe comprising the Zipcode (Zc or ZIP) sequence which is essentially complementary to a corresponding ZipComcode (ZCc or cZIP). The capture probe comprising the Zipcode (or ZIP) sequence may be spotted or synthesized on a specified location on the microarray. The Zipcode (or ZIP) sequence is a unique identifier sequence, which is complementary to the ZipComcode sequence. The present invention relates particularly to microarrays and the use thereof, comprising unique 20 to 30 base oligonucleotides, for instance 20, 21, 22, 23, 24, 25, 26, 27, 28, 29 or 30 base oligonucleotides, named Zipcodes that are coupled to a porous three dimensional substrate at known locations, as described by van Beuningen et al., (2001, Clinical Chemistry 47: 1931-1933), which is specifically incorporated herein by reference. These Zipcodes hybridise specifically to molecules containing sequences that are complementary to the Zipcodes, i.e. the ZipComcodes. By linking these ZipComcodes to fluorescent primers via a ligation-amplification reaction, Zipcode microarrays may be used to detect and identify micro-organisms, such as for example microbial specimens. Because the Zipcodes represent unique artificial sequences, microarrays comprising Zipcodes can be used as a universal platform for molecular recognition simply by changing the gene specific sequences linked to the ZipComcodes.

The detection of label on a specified location on microarray, such as the Pamchip indicates the presence of a hybridisation product between the ligated product and the Zipcode sequence on the microarray.

Accordingly, the present invention relates to a method as described herein, wherein said capture probe hybridises specifically to a corresponding ZipComcode. The amplified target nucleic acid or nucleic acids hybridised to a corresponding capture probe or probes on a microarray may result in a hybridisation pattern. The hybridisation pattern, including the intensity of hybridisation, may be characteristic for a given micro-organism.

It will be apparent that the present invention relates to a method as described herein, wherein a signal is detected after hybridising the specifically amplified nucleic acids or the ligated probes to the capture probe. The said signal is preferably a fluorescent or phosphorescent signal, and said fluorescent or phosphorescent signal may be detected by a CCD camera or by laser scanning, such as for example an FD10 System® (Olympus) or a Pamalyzer® (PamGene NV). Alternatively, the present invention relates to a method as described herein, wherein said microarray is an Arraytube® and said fluorescent or phosphorescent signal may be detected by a CCD camera and/or laser scanning.

Alternatively, the present invention relates to a method as described herein, wherein the hybridization signal is a colorimetrical signal using biotin labelled primers detected by any method known in the art such as for instance conjugation with horseradish peroxidase-streptavidine followed by a peroxidase coloring reaction. The latter reaction may be visualized using an ArrayTube Reader (Clondiag GMBH, Jena, Germany).

As already mentioned before, the price of a microarray presents the larger cost per test. In order to decrease the price per test, the microarray can be interrogated simultaneously with more than one sample. As such, it is contemplated that each individual sample is subjected to the method of the present invention until the hybridisation step, i.e. from each individual sample, the micro-organisms are captured, after which the nucleic acids are extracted (step a), which subsequently undergo a ligase detection reaction (step b). Next, the amplified target nucleic acids if present are detected (step c) and the positive samples are collectively hybridized to the capture probes on a single microarray (step d) and the hybridized target nucleic acids are detected (step e). The probes pair used per sample may be identical, e.g. detecting the same target nucleic acid, or may differ per sample, e.g. detecting different target nucleic acids. However, in order to differentiate between amplified target nucleic acids from different samples or between different amplified target nucleic acids derived from a single sample, each probe, and thus the amplified target nucleic acid, must be individually assignable and detectable. Hence, each probe comprises a distinct and individually identifiable tag (e.g. identifier region ZIP), such as a particular ZipComcode, complementary to a distinct capture probe on the microarray. Although the nucleic acid probe pairs may detect the same target nucleic acids in different samples, each amplified target nucleic acid derived from each sample is traceable because of its discrete tag, corresponding to a specific address on the microarray. In an alternative embodiment, the probes do not comprise tags, but only the primers used for amplification comprise a distinct and individually identifiable tag, such as a ZCc (or cZIP). Obviously, the same considerations as mentioned above apply, in that the tags should differ per sample, and/or per probe, making each individual sample and/or probe identifiable. Accordingly, the present invention relates to a method as described herein, wherein amplified target nucleic acids derived from at least two samples hybridized to capture probes present on a single microarray.

The person skilled in the art will understand that the ZIP region and its complementary sequence cZIP intend only to reference the complementarity i.e. the ability to hybridize to each other specifically, irrespective of the position of the ZIP and/or cZIP sequence. The capture probe on the microarray may therefore comprise a cZIP, provided that the to be detected molecules comprise the ZIP region.

The data obtained by the methods of the present invention may be further analysed, possibly in an automated fashion. For instance, the hybridisation pattern obtained may be compared to hybridisation patterns stored in a databank. In this regard, the present invention relates also to a computer program stored on computer readable medium capable of performing the comparison of the obtained hybridisation pattern with the hybridisation patterns stored in a databank. Accordingly, the present invention relates to a computer comprising a computer readable medium capable of performing the methods described above. Also, the present invention relates to a computer readable medium comprising a computer program according capable of performing the method described above. Furthermore, the present invention relates to a computer program capable of displaying a web page on a remote computer enabling the use of the method described before.

In a further embodiment, the present invention relates to kits for determining the presence of micro-organisms in a sample comprising the essentials of the methods of the present inventions, for instance, said kits may comprise possibly a filter, possibly means for extracting nucleic acids from said micro-organisms, means for specifically amplifying said nucleic acids, means for detecting the amplified nucleic acids, possibly means for analysing the amplified nucleic acids, e.g. microarrays, such as flow through microarrays, possibly buffers and/or an instruction manual.

The characterisation of mixed microbial populations is not easily achieved by current methods and has wide potential application. In most environments where bacteria are found a complex mixture of species is present which may change as a response to local conditions or evolve time. Classical microbiological methods are generally not well suited to the study of these systems as they rely on culture and subsequent isolation of individual colonies. This may only recover a proportion of the species present and also results in large numbers of isolates, which must be characterised. Molecular methods involving the amplification of conserved genes from complex populations and their subsequent characterisation, by cloning and sequencing, or hybridisation, provide alternatives to culture but remain complex. Additionally the amplification step may also introduce bias.

In actively growing populations of cells, each cell contains many copies of the ribosomal RNAs the specific sequence of which are widely used to identify bacterial species (Woese 1987, Microbiol. Rev. 51:221-271). Due to this natural "amplification" of these sequences within active cells it is possible to detect these sequences without amplification (Small J. et al. 2001 App. Environ. Micro. 67:4708-4716). Here a method is presented for the extraction and direct identification of ribosomal RNA on a three dimensional array surface. This potentially allows the rapid parallel identification of a wide range of species in a sample without the need for enzymatic amplification or labelling. The method presented here demonstrates almost real time monitoring of complex bacterial communities will be possible which will have application in many areas.

Hence, it will be appreciated that the present invention relates to the methods described above, wherein said step of analysing comprises hybridising a stacking probe to the nucleic acids, nucleic acid mixture and/or cDNA, said stacking probe being complementary for a region of 16S, 18S, 23S or 28S rRNA, thereby providing a nucleic acid/stacking probe complex. Said step of analysing may further comprise hybridising said nucleic acid/stacking probe complex to a capture probe, said capture probe being complementary to a region of the nucleic acid different from the nucleic acid/stacking probe complex. Said capture probe may be specific for a micro-organism. The stacking probe may be labelled. The region of 16S, 18S, 23S or 28S rRNA may be conserved (over species).

It will be evident to the person skilled in the art that the present invention relates to the use of a microarray as mentioned herein in the method of the present invention. Also, the present invention relates to the use of at least one pair of a first nucleic acid probe and a second nucleic acid probe as defined supra, including coupled probes, the use of a filter as described above, and/or the use of at least one set of two primers as defined above, in the methods according to the invention.

Before the subject invention is described further, it is to be understood that the invention is not limited to the particular embodiments of the invention described herein, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

The following examples and figures are offered by way of illustration and not by way of limitation. Nevertheless, the content of said examples and figures may be generalised in the concept of the present invention.

EXAMPLES

Example 1

Design of Real-Time Ligation-Amplification Probes

Two ligation-amplification probes were used, named "I" and "II", which have the following design (from 5'-3'), with segments a, b, c, d, e, f, going from the 5'-end to the 3'-end (FIG. 1):

Segment I-a of 20 nucleotides equal to amplification primer 1 (FIG. 1, Eco);

Segment I-b of 24 nucleotides comprising the cZIP-sequence (FIG. 2, cZIP);

Segment I-c of 20-30 nucleotides complementary to the target sequence (FIG. 1, cSeq 2);

Segment II-d of 20-30 nucleotides complementary to the target sequence and located immediately downstream of segment I-c (FIG. 1, cSeq 1)

Segment II-e of 20 nucleotides comprising the DET-sequence (FIG. 1, DET);

Segment II-f of 20 nucleotides complementary to amplification primer 2 (FIG. 1, cMse);

The cZIP sequences are as described in WO-2004-106547.

All probes were ordered at Biolegio B.V. (Nijmegen, The Netherlands).

Eco and Mse refer to the primer binding regions 1 and 2, cEco and cMse refer to their respective complementary sequences. ZIP and cZIP refer to the DNA segments used for microarray detection, where cZIP has the complementary sequence of ZIP. DET and cDET refer to DNA segments used for real time detection during amplification, where cDET has the complementary sequence of DET. cSeq-1 and cSeq-2 refer to DNA segments complementary to the target DNA.

Example 2

Description of Bacterial Strains and DNA Isolation

The following 6 bacterial strains were chosen for real-time LDR

1. *Salmonella enterica* ssp. *enterica* serovar Virchow
2. *Salmonella enterica* ssp. *enterica* serovar Paratyphi B var Java
3. *Escherichia coli*
4. *Enterobacter cloaca*
5. *Shigella flexneri*
6. *Campylobacter jejuni*

Pure cultures were inoculated into nutrient broth and grown o/n at 37° C. 100 µl of this o/n culture was used for DNA isolation using the Qiagen genomic DNA isolation kit according to the procedures advised by the manufacturer (Qiagen, Venlo, The Netherlands).

Example 3

Real-Time Ligase Detection Reactions (FIG. 2)

The amplification primers have the following sequence:

```
Primer 1 (Eco): 5'-biotin-GTAGACTGCGTACCAATTC-3'

Primer 2 (Mse): 5'-GACGATGAGTCCTGAGTAA-3'
```

The primers were ordered at Biolegio B.V. (Nijmegen, The Netherlands); Biotin is covalently attached to the 5' end of primer 1, and was used to detect the amplification products on the microarray.

The ligation reactions were carried out in a volume of 10 µl containing:
- 1.0 fMol of each real-time ligation-amplification probe oligonucleotide
- 0.5 ng of target-DNA of the organisms to be analyzed
- 1 unit Taq DNA ligase (New England Biolabs, Beverly, Mass., U.S.A.)
- 1.0 µl 10× Taq DNA ligase buffer (New England Biolabs, Beverly, Mass., U.S.A.)
- sterile water to an end volume of 10 µl.

23 real-time ligation-amplification probes were used based on the PremiTest *Salmonella* probes (DSM PremiTest, Geleen, The Netherlands; Wattiau et al., Int. J. Food Microbiol., 123 (2008), 293-298), and to which the DET segment IIe is added with the sequence 5'-TCCGATGAGTCG-CAATCCTA-3'. This DET-segment is not added to probes 16, 17, 19, 20, 22 and 23, because these constitute the reaction control probes. In these examples for each probe segments I and II are joined creating single probes with the order IId-IIe-IIf-Ia-Ib-Ic in stead of two separate probe segments.

The ligation reaction was incubated for 30 seconds at 98° C., and subsequently for 16 hours at 55° C. in a Biorad Mycycler (Biorad, Hercules, Calif., U.S.A.).

Subsequently, the real-time amplification reaction was carried out. For this purpose 40 µl of a solution was added containing 10 pMol of primer-1, 10 pMol of primer-2, 2 pMol of Detector molecule D1 with the sequence 5'FAM-TAG-GATTGCGACTCATGCCA-TAMRA-3', 0.5 units Amplitaq DNA polymerase (Applied Biosystems, Foster City, Calif., U.S.A.), 0.25 mM dNTPs (from a 20 mM dNTP-mix, Amersham Biosciences, Piscataway, N.J., U.S.A.) in 20 mM Tris.HCl pH 8.5. The PCR was carried out using the amplification conditions as described by Vos et al., Nucleic Acids Research 23(21), (1995), 4407-4414, using a Biorad iCycler IQ. (Biorad Inc., Hercules, Calif., U.S.A.).

Example 4

Detection and Typing of *Salmonella* in 6 Bacterial Samples Using Real-Time LDR

1. DNA was isolated from the 6 bacterial strains described in example 2;
2. Real-time ligation-amplification reactions were carried out as described in example 3. The reactions yield 6 real-time PCR profiles (see FIG. 3).
3. The reaction products of samples 1, 2 and 3 (two positive and one negative real-time LDR) were hybridized to a Clondiag Array Tube using the "Detection Step" of the PremiTest *Salmonella* protocol (DSM PremiTest, Geleen, The Netherlands).
4. The results are displayed in FIG. 4, and confirm that the 2 real-time positive samples contain *Salmonella* serotypes Virchow and Paratyphi B var Java, respectively. The negative sample yields the array image of a *Salmonella* negative sample displaying the reaction control spots only.

The invention claimed is:

1. A method for determining the presence of micro-organisms in a sample and identifying and characterizing said micro-organisms if present, comprising the steps of:
   (a) extracting nucleic acids from micro-organisms, said nucleic acids comprising target nucleic acids,
   (b) performing a ligase detection reaction (LDR) on said target nucleic acids, comprising:
   (b1) providing a pair of a first nucleic acid probe and a second nucleic acid probe, said first nucleic acid probe comprising a 3' located target-specific sequence I complementary to a distinct part of said target nucleic acid and said second nucleic acid probe comprising a 5' located target-specific sequence II complementary to a second part of said target nucleic acid located adjacent to and 3' from said target-specific sequence I, wherein said first nucleic acid probe further comprises a 5' located primer binding section I (PBS(I)), and said second nucleic acid probe comprises a 3' located primer binding section II (PBS(II));
   (b2) incubating said target nucleic acid with said first nucleic acid probe and said second nucleic acid probe under conditions allowing hybridisation of complementary nucleic acids,
   (b3) connecting any adjacent probes,
   (b4) providing at least one set of two primers, wherein a first primer (primer I) is substantially identical to primer binding section I, and the second primer (primer II) is substantially complementary to primer binding section II, and
   (b5) amplifying any connected probe nucleic acid of step (b3), wherein amplification is initiated by binding of nucleic acid primer specific for a primer binding section, thereby providing amplified target nucleic acids, wherein one or more detector molecules that detect the amplified target nucleic acids, are present in step (b5),
   (c) monitoring the signal of said detector molecule and/or the modulation of the signal of said detector molecule, wherein modulation in the signal of said detector molecule indicates the presence of said target sequence whereby the presence of a microorganism is determined,
   (d) whereby step (c) determines that a microorganism is present, hybridizing the amplified target nucleic acids of step (c) to a capture probe, and,
   (e) detecting the hybridized target nucleic acids of step (d), whereby the micro-organism is identified.

2. The method according to claim 1, wherein hybridizing amplified target nucleic acids of step (d) are target sequences providing a positive signal in step (c).

3. The method according to claim 1, wherein said detector molecules comprise one or more oligonucleotide detector probes having a sequence at least partially complementary to a target nucleic acid sequence to be detected, a fluorescent reporter moiety, and a fluorescent quencher moiety capable of quenching the fluorescence of said reporter moiety, wherein said oligonucleotide probe exists in at least one single-stranded, partially single-stranded or double-stranded conformation when unhybridized, wherein said quencher moiety quenches the fluorescence of said reporter moiety, and wherein said oligonucleotide probe exists in at least one conformation when hybridized to said target nucleic acid where the fluorescence of said reporter moiety is unquenched.

4. The method according to claim 3, wherein said oligonucleotide detector molecules comprise at least one region that is substantially complementary to at least one region of the first nucleic acid probe or at least one region of the second nucleic acid probe.

5. The method according to claim 1, wherein at least one of the first nucleic acid probe and the second nucleic acid probe further comprises at least one detector region DET, wherein the at least one DET is:
  (i) substantially complementary to one or more oligonucleotide detector probes, wherein the one or more oligonucleotide detector probes comprises a sequence cDET complementary with the detector region DET, used for detecting the accumulation of the reaction products during the amplification reaction of step (b5);
  (ii) substantially non-complementary to said target nucleic acid; and
  (iii) located in between the target sequence and the primer binding section.

6. The method according to claim 1, wherein at least two groups of pairs of first and second nucleic acid probes are provided, wherein each group of first and second nucleic acid probes hybridises to a specific target nucleic acid, and comprises a specific primer binding site I and/or II.

7. The method according to claim 1, wherein at least two groups of pairs of first and second nucleic acid probes are provided, wherein each group of first and second nucleic acid probes hybridises to a specific target nucleic acid, and the first or second nucleic acid probe of each group comprises a specific identifier region.

8. The method according to claim 7, wherein said identifier region comprises a cZIP or ZIP, and wherein the identifier region is located in between the target-specific sequence and the primer binding sequence.

9. The method according to claim 1, wherein said first nucleic acid probe is coupled with its 5' end to the 3' end of said second nucleic acid probe.

10. The method according to claim 1, wherein said connecting step (b3) comprises the use of a ligase.

11. The method according to claim 1, wherein the amplified target nucleic acid is labelled during amplification.

12. The method according to claim 1, wherein said capture probe comprises a region ZIP which is substantially complementary to a corresponding identifier region cZIP on the first nucleic acid probe and/or the second nucleic acid probe, or wherein said capture probe comprises a region cZIP which is substantially complementary to a corresponding identifier region ZIP on the first nucleic acid probe and/or the second nucleic acid probe.

13. The method according to claim 1, wherein:
  (a) said first nucleic acid probe comprises from 5' to 3': a Primer Binding Sequence I (PBS(I)), cZIP, and a target specific sequence I (tss(I)), said second nucleic acid probe comprises from 5' to 3': a target specific sequence II (tss(II)), DET and a Primer Binding Sequence II (PBS(II));
  (b) said first nucleic acid probe comprises from 5' to 3': a PBS(I), DET, and tss(I), said second nucleic acid probe comprises from 5' to 3': a tss(II), cZIP and PBS(II);
  (c) said first nucleic acid probe comprises from 5' to 3': a PBS(I), cDET and tss(I), said second nucleic acid probe comprises from 5' to 3': a tss(II), cZIP and PBS(II);
  (d) said first nucleic acid probe comprises from 5' to 3': a PBS(I), cZIP, DET and tss(I), said second nucleic acid probe comprises from 5' to 3': a tss(II) and PBS(II);
  (e) said first nucleic acid probe comprises from 5' to 3': a PBS(I), cZIP, cDET, and tss(I), said second nucleic acid probe comprises from 5' to 3': a tss(II) and PBS(II);
  (f) said first nucleic acid probe comprises from 5' to 3': a PBS(I), DET, cZIP and tss(I), said second nucleic acid probe comprises from 5' to 3': a tss(II) and PBS(II);
  (g) said first nucleic acid probe comprises from 5' to 3': a PBS(I), cDET, cZIP and tss(I), and said second nucleic acid probe comprises from 5' to 3': a tss(II) and PBS(II);
  (h) said first nucleic acid probe comprises from 5' to 3': a PBS(I) and tss(I), said second nucleic acid probe comprises from 5' to 3': a tss(II), DET, cZIP and PBS(II);
  (i) said first nucleic acid probe comprises from 5' to 3': a PBS(I) and tss(I), said second nucleic acid probe comprises from 5' to 3': a tss(II), cZIP, DET and PBS(II);
  (j) said first nucleic acid probe comprises from 5' to 3': a PBS(I), ZIP and tss(I), and said second nucleic acid probe comprises from 5' to 3': a tss(II), DET and PBS(II);
  (k) said first nucleic acid probe comprises from 5' to 3': a PBS(I), cZIP, DET and tss(I), said second nucleic acid probe comprises from 5' to 3': a tss(II) and PBS(II);
  (l) said first nucleic acid probe comprises from 5' to 3': a PBS(I), ZIP, cDET and tss(I), and said second nucleic acid probe comprises from 5' to 3': a tss(II) and PBS(II);
  (m) said first nucleic acid probe comprises from 5' to 3': a PBS(I), DET, ZIP and tss(I), said second nucleic acid probe comprises from 5' to 3': a tss(II) and PBS(II); and/or,
  (n) said first nucleic acid probe comprises from 5' to 3': a PBS(I), cDET, ZIP and tss(I), and said second nucleic acid probe comprises: a tss(II) and PBS(II).

14. The method of claim 13, wherein primer 1 is labeled in (a)-(i) and/or primer II is labeled in (j)-(n).

15. The method according to claim 1, wherein said capture probe is spatially addressable on a microarray.

16. The method according to claim 1, wherein the amplified target nucleic acids derived from at least two samples are hybridised to capture probes present on a single microarray.

17. The method according to claim 1, wherein the amplified target nucleic acids hybridizes to the corresponding capture probes on a microarray resulting in a hybridization pattern.

18. The method of claim 1, wherein at least one of the first nucleic acid probe and the second nucleic acid probe further comprises at least one identifier region, wherein the identifier region corresponds to a region of a capture probe, wherein the identifier region is substantially non-complementary to said target nucleic acid, and wherein the identifier region is located in between the target specific sequence and the primer binding section of the nucleic acid probe.

19. The method of claim 1, where in at least one of the first nucleic acid probe and the second nucleic acid probe comprises a stuffer.

* * * * *

SEQUENCE LISTING

```
<160> NUMBER OF SEQ ID NOS: 4

<210> SEQ ID NO 1
<211> LENGTH: 19
<212> TYPE: DNA
<213> ORGANISM: Artificial
<220> FEATURE:
<223> OTHER INFORMATION: Primer 1 (ECO)
<220> FEATURE:
<221> NAME/KEY: misc_feature
<222> LOCATION: (1)..(1)
<223> OTHER INFORMATION: g attached to biotin

<400> SEQUENCE: 1 gtagactgc gtaccaattc                                              19

<210> SEQ ID NO 2
<211> LENGTH: 19
<212> TYPE: DNA
<213> ORGANISM: Artificial
<220> FEATURE:
<223> OTHER INFORMATION: Primer 2 (Mse)
```

```
<400> SEQUENCE: 2
gacgatgagt cctgagtaa                                              19

<210> SEQ ID NO 3
<211> LENGTH: 20
<212> TYPE: DNA
<213> ORGANISM: Artificial
<220> FEATURE:
<223> OTHER INFORMATION: Probe DET-segment

<400> SEQUENCE: 3
tccgatgagt cgcaatccta                                             20

<210> SEQ ID NO 4
<211> LENGTH: 20
<212> TYPE: DNA
<213> ORGANISM: Artificial
<220> FEATURE:
<223> OTHER INFORMATION: Probe
<220> FEATURE:
<221> NAME/KEY: misc_feature
<222> LOCATION: (1)..(1)
<223> OTHER INFORMATION: t attached to FAM
<220> FEATURE:
<221> NAME/KEY: misc_feature
<222> LOCATION: (20)..(20)
<223> OTHER INFORMATION: a attached to TAMRA

<400> SEQUENCE: 4
taggattgcg actcatgcca                                             20
```